United States Patent [19]

Murakami et al.

[11] Patent Number: 5,055,464
[45] Date of Patent: Oct. 8, 1991

[54] BENZOLACTAM COMPOUNDS AND PHARMACEUTICAL USES THEREOF

[75] Inventors: Shu Murakami, Fukuoka; Tsuguo Ikebe, Oita; Ichiro Hakamada, Oita; Koretake Anami, Oita, all of Japan

[73] Assignee: Yoshitomi Pharmaceutical Industries Ltd., Osaka, Japan

[21] Appl. No.: 471,023

[22] Filed: Jan. 25, 1990

Related U.S. Application Data

[63] Continuation-in-part of Ser. No. 291,898, Dec. 29, 1988, abandoned.

[30] Foreign Application Priority Data

Dec. 29, 1987 [JP] Japan .................. 62-336074

[51] Int. Cl.$^5$ .................. A61K 31/55; C07D 281/10
[52] U.S. Cl. .................. 514/211; 514/213; 514/281; 514/183; 540/490; 540/491; 540/517; 540/523
[58] Field of Search .................. 540/490, 491, 517, 523; 514/211, 213, 281, 183

[56] References Cited

U.S. PATENT DOCUMENTS

| | | | |
|---|---|---|---|
| 4,564,612 | 1/1986 | Sugihara et al. | 540/491 |
| 4,692,522 | 9/1987 | Parsons et al. | 540/523 |
| 4,739,066 | 4/1988 | Sugihara et al. | 540/491 |
| 4,767,756 | 8/1988 | Das et al. | 540/523 |

FOREIGN PATENT DOCUMENTS

| | | | |
|---|---|---|---|
| 2103614 | 2/1985 | United Kingdom | 540/523 |
| 2143816 | 2/1985 | United Kingdom | 540/491 |

OTHER PUBLICATIONS

Derwent Publication—Abstract of Japanese Unexamined Publication 1148171/86.

Primary Examiner—Robert T. Bond
Attorney, Agent, or Firm—Sughrue, Mion, Zinn, Macpeak & Seas

[57] ABSTRACT

Benzolactam compounds of the general formula

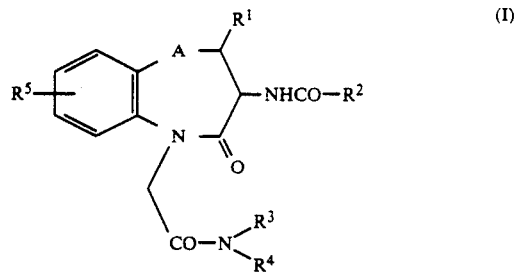

or isomers thereof as well as salts thereof inclusive of hydrates and/or solvates forms thereof, and benzolactam compounds of the general formula

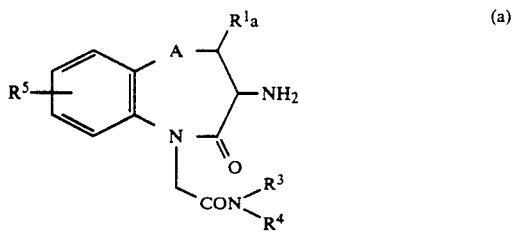

and

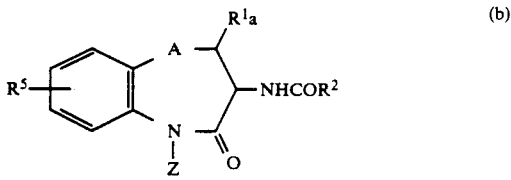

wherein each of the symbols is as defined in the specification.

The compound (I) exhibit antiamnesic activity, and are useful as brain function-improving drugs. The compounds (a) and (b) are useful as an intermediate for said compounds (I). Futher, the compound (a) show diuretic or antiulcer activity, and are useful as a diuretic or antiulcer agent.

8 Claims, No Drawings

BENZOLACTAM COMPOUNDS AND PHARMACEUTICAL USES THEREOF

CROSS-REFERENCE TO RELATED APPLICATIONS

This application is a Continuation-in-Part application of Ser. No. 07/291,898 filed on Dec. 29, 1988, now abandoned.

BACKGROUND OF THE INVENTION

This invention relates to novel benzolactam compounds which are useful as pharmaceuticals, particularly as brain function-improving drugs, or isomers thereof as well as salts thereof, their pharmaceutical uses and the intermediates for their synthesis.

In European Patent Publication No. 125056A, European Patent Publication No. 156455A, British Patent Publication No. 2143816A and Japanese Patent Unexamined Publication (Kokai) No. 148171/1986, there are disclosed 3-(1-carboxyalkyl)amino-4-oxo-2,3,4,5-tetrahydro-1,5-benzothiazepine-5-acetic acid derivatives which possess antihypertensive actions. In British Patent Publication No. 2103614A and European Patent Publication No. 166357A, there are reported 3-amino-2-oxo-2,3,4,5-tetrahydro-1H-1-benzazepine derivatives which possess antihypertensive actions or cholecystokinin antagonistic actions.

A number of psychotropic agents and antidemential agents called consciousness disturbance-improving drugs, antiamnesiac drugs, cognition-activating drugs or nootropics have been developed so far in order to improve consciousness-disturbance, remembrance-disturbance, cognition-deterioration, hypobulia and various dementia which are caused by brain function disturbance or brain organ disturbance. Any of those drugs, however, are not necessarily satisfactory in the aspect of their efficacy, duration of their actions and their side effects.

As the result of intensive research conducted by the present inventors to solve the above-mentioned problems, they found that novel benzolactam compounds exhibit an improving effect on various experimental amnesia models, socalled antiamnesia actions, which led to the accomplishment of the present invention.

SUMMARY OF THE INVENTION

Accordingly, it is the object of the present invention to provide novel benzolactam compounds possessing antiamnesia activity.

Another object of the present invention is to provide a pharmaceutical use of said benzolactam compounds.

A further object of the invention is to provide a novel benzolactam compounds which are useful as an intermediate for manufacturing the benzolactam compounds of the present invention.

Moreover, the present invention provides a novel benzolactam compound which is useful as a diuretic agent or an antiulcer agnet.

DETAILED DESCRIPTION

This invention relates to benzolactam compounds of the general formula

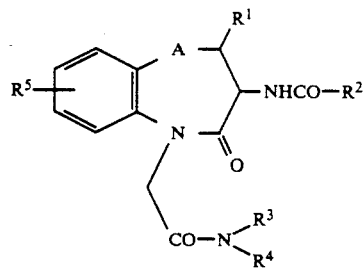

(I)

wherein A is sulfur atom, oxygen atom, methylene group, —$NR^6$— group (wherein $R^6$ is hydrogen atom, an alkyl group, an aralkyl group or an amino-protecting group) or carbonyl group; $R^1$ is hydrogen atom, an alkyl group, a cycloalkyl group, an aralkyl group, an aryl group, a heteroaryl group or a heteroaralkyl group; $R^2$ is an alkyl group, a cycloalkyl group, an aralkyl group, a halogenated alkyl group, an alkoxy group, an aryl group, a heteroaryl group, a heteroaralkyl group or a heterocyclic group substituted by oxo group; $R^3$ and $R^4$ are the same or different and are independently hydrogen atom, an alkyl group, an aralkyl group or groups which are combined with each other together with the adjacent nitrogen atom to form a heterocycle; and $R^5$ is hydrogen atom or one to three halogen atom(s), alkyl group(s) or alkoxy group(s) (when $R^5$ is two to three atoms and/or groups, the atoms and/or the groups are the same or different), and their various isomers and their salts.

The present invention also relates to a pharmaceutical composition which comprises the compound of the general formula (I) and a pharmaceutically acceptable additive.

Further, the present invention relates to compounds of the general formula

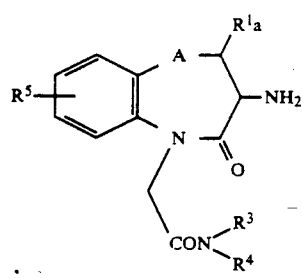

(a)

wherein $R^{1a}$ is the alkyl group, the cycloalkyl group, the aralkyl group, the aryl group, the heteroaryl group or the heteroaralkyl group in the definitions of $R^1$, and other symbols are as defined above, and compounds of the general formula

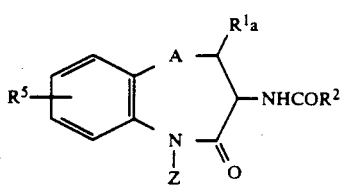

(b)

wherein Z is hydrogen atom or a group of the formula: —$CH_2CO_2Q$, wherein Q is a carboxy-protecting group such as an alkyl group or an aralkyl group, and other symbols are as defined above, or an isomer thereof as well as a salt thereof which are useful as important intermediates for manufacturing the compounds of the general formula (I).

Further, the compounds of formula (a) exhibit diuretic or antiulcer activity, and are useful as a diuretic or an antiulcer agent.

The respective definition of the symbols throughout the present specification including the general formula (I) for the compound of the present invention is in further detail explained hereafter. The alkyl group represented by $R^1$, $R^2$, $R^3$, $R^4$, $R^5$ and $R^6$ is an alkyl group having 1 to 6 carbon atoms such as methyl, ethyl, propyl, isopropyl, butyl, isobutyl, tert-butyl, pentyl, isopentyl, neopentyl or hexyl, which may have unsaturated bond (double bond, triple bond). The cycloalkyl group represented by $R^1$ and $R^2$ is a cycloalkyl group having 5 to 7 carbon atoms such as cyclopentyl, cyclohexyl or cycloheptyl, which may contain a double bond on the ring. The aryl group represented by $R^1$ and $R^2$ is phenyl, 1-naphthyl or 2-naphthyl which may have on the aromatic ring at least one substituent selected from among halogen (e.g., fluorine, chlorine, bromine), trifluoromethyl, hydroxy, amino, nitro, cyano, an alkyl group having 1 to 6 carbon atoms and an alkoxy group having 1 to 6 carbon atoms (e.g., methoxy, ethoxy, propoxy, isopropoxy, butbxy, tert-butoxy, pentyloxy, isopentyloxy, hexyloxy). The aralkyl group represented by $R^1$, $R^2$, $R^3$, $R^4$ and $R^6$ is an alkyl group having 1 to 6 carbon atoms substituted at least one of the above-mentioned aryl groups, which is exemplified by benzyl, diphenylmethyl, 1-phenylethyl, 2-phenylethyl, 3-phenylpropyl, 4-phenylbutyl and 6-phenylhexyl. The heteroaryl group represented by $R^1$ and $R^2$ is a monocyclic or polycyclic aromatic ring containing 1 to 3 nitrogen atom(s), oxygen atom(s) and/or sulfur atom(s) such as thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms. The heteroaralkyl group represented by $R^1$ and $R^2$ is an alkyl group having 1 to 6 carbon atoms which is substituted by at least one heteroaryl group as mentioned above, which is exemplified by 2-thienylmethyl, 3-thienylmethyl, 2-furylmethyl, 3-furylmethyl, 2-pyridylmethyl, 3-pyridylmethyl, 4-pyridylmethyl, 2-indolylmethyl and 3-indolylmethyl. The alkoxy group represented by $R^2$ and $R^5$ is an alkoxy group having 1 to 6 carbon atoms as mentioned above, which may be substituted by an aryl group. As the halogenated alkyl group represented by $R^2$, there can be mentioned trifluoromethyl, chloromethyl, 2,2,2-trifluoroethyl and the like. The heterocycle substituted by an oxo group in respect to $R^2$ is representable by the formula

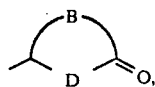

wherein B is an alkylene group (an alkylene having 1 to 6 carbon atoms such as methylene, ethylene, trimethylene, propylene, tetramethylene, hexamethylene, etc.) which may further be substituted by an alkyl group having 1 to 4 carbon atoms such as methyl or ethyl, an alkylidene group (propylidene, butylidene), an alkenylene group (vinylene, propenylene, etc.), —CH$_2$OCH$_2$—, —CH$_2$S(O)$_n$CH$_2$— (n represents an integer of 0 to 2), —CH$_2$CON(R$^8$)— (wherein R$^8$ is hydrogen atom or an alkyl group having 1 to 6 carbon atoms) and D is an oxygen atom, methylene group or —N(R$^9$)— (wherein R$^9$ is a hydrogen atom or an alkyl group having 1 to 6 carbon atoms). The heterocycle may be fused with an aryl or a heteroaryl group. Examples of the heterocycle formed by $R^3$ and $R^4$ which are combined with each other include 1-pyrrolidinyl, piperidino, morpholino and 1-piperazinyl, which may be substituted by an alkyl, an aralkyl and the like. The halogen atom represented by $R^5$ includes fluorine, chlorine and bromine as mentioned above. The amino-protecting group represented by $R^6$ includes benzyloxycarbonyl, tert-butoxycarbonyl, trifluoroacetyl and so on.

The compounds of the above-mentioned general formula (I) have 1 to 3 asymmetric atom(s) in the molecule. Thus, in the case where they have an asymmetric atom, there exist optical isomers, their racemic isomers or their mixtures. In case where they have at least 2 asymmetric atoms, there can exist optically pure diastereomers, racemic isomers of diastereomers or mixtures of diastereomers. The present invention encompasses all forms of these stereoisomers.

The compounds and their various isomers of the present invention can form acid addition salts with inorganic acids or organic acids, and also can exist as their hydrates (e.g. monohydrate, hemihydrate, dihydrate, sesquihydrate) or their solvates with, for example, ethanol, isopropyl alcohol or dimethylformamide. The present invention includes these salts, hydrates and solvates.

Preferable compounds of the general formula (I) are trans-3(S)-[γ-butyrolactone-γ(S)-carboxamido]-4-oxo-2(R)-phenyl-2,3,4,5-tetrahydro-1,5-benzothiazepine-5-acetamide, trans-3(R)-[γ-butyrolactone-γ(S)-carboxamido]-4-oxo-2(S)-phenyl-2,3,4,5-tetrahydro-1,5-benzothiazepine-5-acetamide, cis-3-[γ-butyrolactone-γ(S)-carboxamido]-4-oxo-2-phenyl-2,3,4,5-tetrahydro-1,5-benzothiazepine-5-acetamide, trans-4-oxo-3-[5-oxo-2(S)-pyrrolidinecarboxamido]-2-phenyl-2,3,4,5-tetrahydro-1,5-benzothiazepine-5-acetamide, trans-3-(2-indolecarboxamido)-4-oxo-2-phenyl-2,3,4,5-tetrahydro-1,5-benzothiazepine-5-acetamide, trans-3-(4,5-dihydroorotylamino)-4-oxo-2-phenyl-2,3,4,5-tetrahydro-1,5-benzothiazepine-5-acetamide, 2-isopropyl-3-(2-indolecarboxamido)-4-oxo-2,3,4,5-tetrahydro-1,5-benzothiazepine-5-acetamide, 3(R)-[γ-butyrolactone-γ(S)-carboxamido]-4-oxo-2,3,4,5-tetrahydro-1,5-benzothiazepine-5-acetamide, trans-3-[γ-butyrolactone-γ(S)-carboxamido]-4-oxo-2-(2-thienyl)-2,3,4,5-tetrahydro-1,5-benzothiazepine-5-acetamide, trans-3-(2-indolecarboxamido)-4-oxo-2-(2-thienyl)-2,3,4,5-tetrahydro-1,5-benzothiazepine-5-acetamide, trans-3-(2-indolecarboxamido)-4-oxo-2-phenyl-N-(2-phenylethyl)-2,3,4,5-tetrahydro-1,5-benzothiazepine-5-acetamide, trans-3-(2-indolecarboxamido)-2-phenyl-5-(1-pyrrolidinylcarbonylmethyl)-2,3-dihydro-1,5-benzothiazepin-4(5H)-one, cis-4-oxo-3(R)-[5-oxo-2(S)-pyrrolidinecarboxamido]-2(R)-phenyl-2,3,4,5-tetrahydro-1,5-benzothiazepine-5-acetamide, cis-4-oxo-3(S)-[5-oxo-2(S)-pyrrolidinecarboxamido]-2(S)-phenyl-2,3,4,5-tetrahydro-1,5-benzothiazepine-5-acetamide, cis-3-[γ-butyrolactone-γ(S)carboxamido]-8-chloro-4-oxo-2-phenyl-2,3,4,5-tetrahydro-1,5-benzothiazepine-5-acetamide, trans-3-[γ-butyrolactone-γ(S)carboxamido]-8-chloro-4-oxo-2-phenyl-2,3,4,5-tetrahydro-1,5-benzothiazepine-5-acetamide, cis-3-(2-indolecarboxamido)-2- oxo-4-phenyl-2,3,4,5-tetrahydro-1H-1-benzazepine-1-acetamide and trans-3-(2-indolecarboxamido)-2-oxo-4-phenyl-2,3,4,5-tetrahydro-1H-1-benzazepine-1-acetamide, or an isomer as well as a pharmaceutically acceptable salt thereof.

Also, preferably compounds of formula (I) are 3(R)-[3-cyclopentanone-1(R)-carboxamido]-4-oxo-2(S)-phenyl-2,3,4,5-tetrahydro-1,5-benzothiazepine-5-acetamide and cis-8-chloro-3-[3-cyclopentanone-1(R)-carboxamide]-4-oxo-2-phenyl-2,3,4,5-tetrahydro-1,5-benzothiazepine-5-acetamide, or an isomer thereof as well as an acid addition salt thereof.

The compound of the general formula (I) can be produced by reacting a carboxylic acid of the general formula

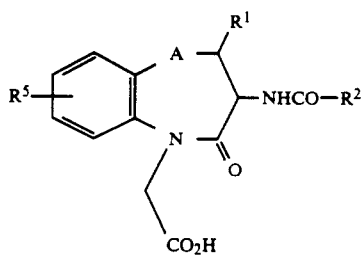

wherein all the symbols are as defined above, or a reactive derivative thereof with a compound of the general formula

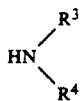

wherein each of the symbols is as defined above, by reacting a compound of the general formula

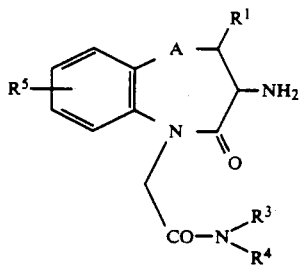

wherein each of the symbols is as defined above, with a carboxylic acid of the general formula

R²COOH (V)

wherein R² is as defined above, or a reactive derivative thereof; or by subjecting a compound of the general formula

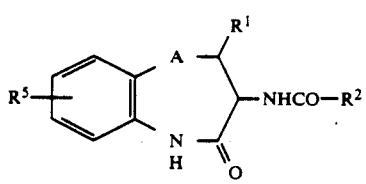

wherein each of the symbols is as defined above, and a compound of the general formula

wherein R³ and R⁴ are as defined above and X is a halogen atom such as chlorine, bromine or iodine, to condensation reaction.

The above-mentioned amidation reaction can be carried out in accordance with a per se known amidation method or peptide synthesis method. For example, when the compound of the general formula (II) or of the general formula (V) is in the free carboxylic acid, form the amidation reaction can be conducted in the presence of a condensating agent such as dicyclohexylcarbodiimide, a phosphorus halide (phosphorus trichloride, phosphorus oxychloride, etc.), diphenylphosphorylazide, 2-chloro-N-methylpyridinium iodide-tributylamine (Mukaiyama Method) in an inert solvent or without any solvent under cooling or at room temperature or under heating.

When the compound of the general formula (II) or the compound of the general formula (V) is employed in the form of an acid halide (acid chloride, acid bromide, etc.), or a mixed acid anhydride (a mixed acid anhydride with a lower alkyl carbonic acid, a mixed acid anhydride with an alkyl phosphoric acid, etc.) as the reactive derivative thereof, the reaction is conducted, preferably, in the presence of an acid scavenger selected from among organic bases such as triethylamine, pyridine and dimethylaniline and inorganic bases such as alkali hydrogencarbonates, alkali carbonates, and alkali hydroxides, in an inert solvent or without any solvent under cooling or heating. Furthermore, when a lower alkyl ester (methyl ester, ethyl ester, etc.) or a so-called active ester (p-nitrophenyl ester, p-nitrobenzyl ester, p-chlorophenyl ester, succinimido ester, benzotriazole ester, etc.) is employed as the reactive derivative, the reaction is conducted in an inert solvent or without any solvent, if desired, in the presence of a strong base catalyst such as sodium alkoxide, at room temperature or under heating.

As inert solvents usable for the above-mentioned amidation reaction, there can be mentioned hydrocarbons such as hexane, benzene and toluene, halogenated hydrocarbons such as chloroform, dichloromethane and dichloroethane, ethers such as tetrahydrofuran and dioxane, esters such as ethyl acetate, ketones such as acetone, alcohols such as methanol, ethanol and isopropyl alcohol, amides such as dimethylformamide and dimethylacetamide, acetonitrile, dimethyl sulfoxide and water, from among which an adequate inert solvent can be selected in accordance with the reaction.

The condensation reaction of the compound of the formula (VI) and the compound of the formula (VII) can be conducted in the presence of an acid scavenger in an inert solvent under cooling to under heating. The acid scavenger usable for the reaction is exemplified by alkali metal carbonates such as sodium carbonate and potassium carbonate, alkali metal hydrogencarbonates such as sodium hydrogencarbonate, alkali metal hydrides such as sodium hydride and lithium hydride, alkali metal alkoxides such as sodium methoxide, sodium ethoxide and potassium tert-butoxide and organic bases such as triethylamine and pyridine. When the reaction is conducted in a mixture of water and other organic solvent with the use of a phase transfer catalyst such as tetra-n-butylammonium bromide or benzyltriethylammonium iodide, an alkali metal hydroxide such as sodium hydroxide or potassium hydroxide can be employed.

The novel compounds of the general formulae (II), (IV) and (VI) to be used for the above-mentioned amidation reaction and condensation reaction can be produced, for example, in the following manner.

Namely, the compound of the general formula (II) can be obtained by condensation reaction of the compound of the general formula (VI) with the compound of the general formula

$XCH_2CO_2Q$    (VIII)

wherein X and Q are as defined above, in the presence of an acid scavenger as mentioned above in an inert solvent to derive the compound of the general formula

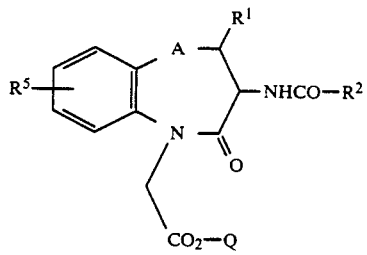

wherein each of the symbols is as defined above, followed by elimination of the carboxyl group-protecting group Q from the compound of the general formula (II').

The deprotection reaction for the carboxyl group-protecting group of the compounds of the formula (II') can be conducted by a conventional method in the organic synthetic chemistry such as treatment with an acid (hydrochloric acid, hydrobromic acid, hydrogen bromide-acetic acid, trifluoroacetic acid, etc.) or an alkali (sodium hydroxide, potassium hydroxide, etc.) or catalytic hydrogenolysis with the use of a catalyst such as palladium carbon or platinum oxide.

The compound of the general formula (IV) can be synthesized by reacting the compound of the general formula

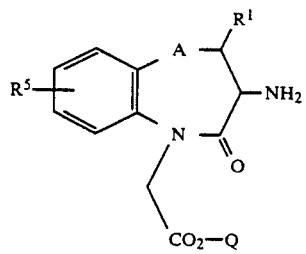

wherein each of the symbols is as defined above, which can be obtained by selective deprotection reaction for the aminoprotecting group of the compound of the general formula (II') wherein $R^2CO$-group is an aminoprotecting group (e.g. trifluoroacetyl, chloroacetyl, ethoxycarbonyl, benzyloxycarbonyl, tert-butoxycarbonyl, etc.) with the compound of the general formula (III).

The compound of formula (X) can be also synthesized by reacting the compound of the general formula

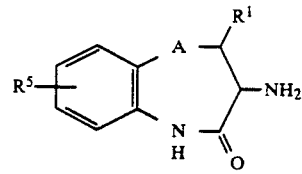

wherein each of the symbols is as defined above, with the compound of the general formula

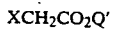

$XCH_2CO_2Q'$    (VIII')

wherein X is as defined above and Q' is the carboxyl-protecting group in the symbol of Q, in the same manner as the above-mentioned condensation reaction.

Also, the compound of the general formula (IV) can be produced by deprotection for the amino-protecting group of the compound of the general formula (I) wherein $R^2CO$-group is an amino-protecting group as mentioned above.

The amidation reaction of the compound of the general formula (X) with the compound of the general formula (III) is essentially the same as the reaction of the ester compound of the compound of the general formula (II) with the compound of the general formula (III), and the reaction can be carried out in a suitable solvent or without any solvent under ordinary pressure or under pressure under cooling or under heating.

The deprotection reaction for the amino-protecting group of the compounds (II'), (I) and (VI) can be easily conducted by a known method such as treatment with an acid (hydrofluoric acid, hydrochloric acid, hydrogen chloride-dioxane, hydrobromic acid, hydrobromic acid-acetic acid, trifluoroacetic acid, etc.) or an alkali (sodium hydroxide, potassium hydroxide, ammonia, etc.) or catalytic hydrogenolysis with the use of a catalyst such as palladium carbon and platinum oxide.

Among the compounds of the general formula (VI) which are starting compounds of the present invention, the compound of the general formula (VI) wherein A is sulfur atom, oxygen atom or —$NR^6$— group (wherein $R^6$ is as defined above) can be synthesized by deriving the compound of the general formula

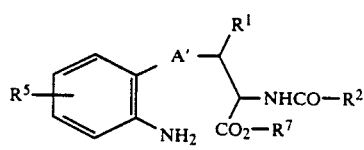

wherein $R^7$ is hydrogen atom, a carboxy-protecting group such as a lower alkyl (e.g. methyl, ethyl or tert-butyl), trimethylsilyl or an aralkyl (e.g. benzyl), A' is sulfur atom, oxygen atom or —$NR^6$— group (wherein $R^6$ is as defined above) and each of the other symbols is as defined above, by addition reaction of the compound of the general formula

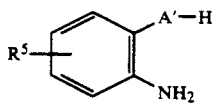

(XII)

wherein $R^5$ and $A'$ are as defined above, to the α-dehydroamino acid derivative of the general formula

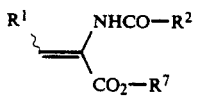

(XI)

wherein each of the symbols is as defined above, and subjecting the thus-obtained compound of the general formula (XIII) to cyclization reaction.

The addition reaction proceeds without solvent or in a suitable solvent such as an alcohol, dimethylformamide, dimethyl sulfoxide, tetrahydrofuran, pyridine without catalyst or in the presence of a basic catalyst such as triethylamine, sodium carbonate or potassium carbonate under cooling or at room temperature or under heating.

The cyclization reaction can be conducted in the presence of or in the absence of a dehydrating or condensating agent without any solvent or in the presence of an inert solvent under cooling or at room temperature or under heating.

The compound of the general formula (VI) can also be synthesized by causing direct addition-cyclization reaction of the compound of the general formula (XI) with the compound of the general formula (XII) without any solvent or in a suitable solvent in the presence of or in the absence of an inorganic acid such as hydrochloric acid or sulfuric acid or an organic acid such as acetic acid, methanesulfonic acid or p-toluenesulfonic acid under heating.

It is needless to say that the compound of the general formula (VI) can be produced also by subjecting the compound of the general formula (IX) and the compound of the general formula (V) to amidation reaction in the same manner as mentioned above.

Meanwhile, the compound of the general formula (IX) which is a starting compound of the present invention can be produced by subjecting the compound of the general formula (VI) wherein —$R^2CO$— group is the above-mentioned amino-protecting group, to deprotection reaction for amino-protecting group, or by the method described below. That is, the compound of the general formula

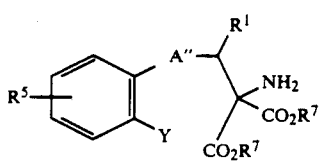

(XVII)

wherein $A''$ is sulfur atom, oxygen atom, a methylene group or —$NR^6$— group (wherein $R^6$ is as defined above), Y is amino or nitro, and each of the other symbols is as defined above, can be produced by deriving the compound of the general formula

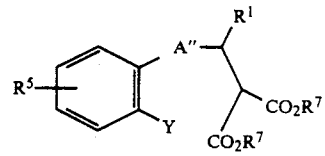

(XVI)

wherein each of the symbols is as defined above, by addition reaction of the compound of the general formula

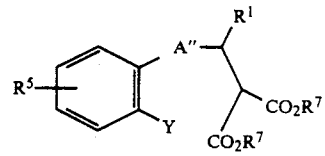

(XV)

wherein $R^5$, $A''$ and Y are as defined above, to the compound of the general formula

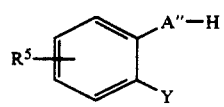

(XIV)

wherein $R^1$ and $R^7$ are as defined above, which can be prepared in accordance with a method analogous to the known method, and subjecting the thus-obtained compound of the general formula (XVI) to amination reaction. The compounds of the general formulae (XVI) and (XVII) wherein Y is amino can be derived by subjecting the compounds of the general formulae (XVI) and (XVII) wherein Y is nitro to reduction. In addition, the compound of the general formula (IX) can be produced by deriving the compound of the general formula

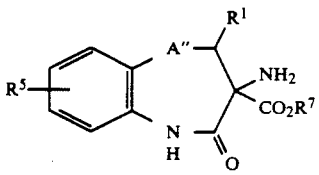

(XVIII)

wherein each of the symbols is as defined above, by ring closure reaction of the compound of the general formula (XVII) wherein Y is amino and subsequently subjecting the compound of the general formula (XVIII) to decarboxylation reaction.

The compound of the general formula (IX) can also be produced by the method described below. That is, the compound of the general formula

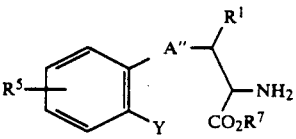

(XIX)

wherein each of the symbols is as defined above, is derived by subjecting the compound of the general formula (XVII) to decarboxylation reaction. The compound of the general formula (XIX) wherein Y is nitro is converted into the compound of the general formula (XIX) wherein Y is amino by further reduction. The compound of the general formula (IX) can be produced by subjecting the thus-obtained compound of the general formula (XIX) wherein Y is amino to ring closure reaction.

The addition reaction of the compounds (XIV) and (XV) proceeds without solvent or in a suitable solvent which does not interfere with the reaction under cooling or at room temperature or under heating. According to the properties of the compounds (XIV) and (XV), there may be used a base such as sodium hydride, butyl lithium, diisopropylamide, lithium sodium alkoxide, etc., an inorganic acid such as hydrochrolic acid, sulfuric acid, etc., an organic acid such as acetic acid, methanesulfonic acid, p-toluenesulfonic acid, etc., or Louis acid such as boron trifluoride, zinc chloride, alminium chloride, titanium tetrachloride, tin (IV) chloride and so on to give preferable results.

The amination reaction of the compound (XVI) proceeds in a solvent which does not interfere with the reaction using a suitable base and an aminating agent. The base used in this reaction can be selected according to the properties of the compound (XVI), examples of which are sodium hydride, lithium diisopropylamide, lithium butylate, sodium alkoxide, sodium hydroxide and so on. As an aminating agent, there may be used O-2, 4-dinitrophenylhydroxylamine, O-mesitylenesulfonylhydroxylamine, O-mesitoylhydroxylamine and so on.

The reduction for the compounds (XVI), (XVII) and (XIX) wherein Y is nitro proceeds in a suitable solvent which does not interfere with the reaction in the presence of a reducing agent. The reduction reaction can be conducted by a method analogous to the known method in the organic chemistry such as catalytic hydrogen reduction with the use of a catalyst such as platinum, palladium, Raney-nickel, rhodium, etc. or a mixture thereof with a carrier; reduction of iron, zinc, etc. with an acid such as hydrochloric acid, acetic acid, etc.; reduction with the use of tin (II) chloride; and so on. Further, the closed circular compounds (XVIII) and (IX) can be respectively produced without isolating reduced body [the general formulae (XVII) or (XIX) wherein Y is amino] by heating the reaction mixture to a suitable temperature in the process of reduction for the compound (XVII) or (XIX).

The decarboxylation reaction for the compounds (XVII) and (XVIII) proceeds in an inert solvent such as pyridine, dimethylformamide, tetrahydrofuran, toluene, xylene, mesitylene, methyl cellosolve, dioxane, methanol, ethanol, isopropanol and water or in a solvent prepared by combining them appropriately in the presence of a base such as sodium hydroxide, potassium hydroxide, etc., an acid such as hydrochloric acid, sulfuric acid, etc., or a decarboxylating agent such as lithium iodide, lithium bromide, lithium chloride, etc. at a temperature of 0° C. to 250° C.

The ring closure reaction for the compounds (XVII) and (XIX) wherein Y is amino proceeds in the presence or in the absence of dehydrating-condensing agent without solvent or in a suitable solvent such as acetic acid, pyridine, dimethylformamide, tetrahydrofuran, toluen, xylene, etc. under cooling or at room temperature or under heating.

It is needless to say that the compound of the general formula (X) can be produced by deprotection reaction for the amino-protecting group of the compound of the general formula (II′) wherein R²CO— is the above-mentioned amino-protecting group. Additionally, the compound of the general formula (X) can be produced by deriving the compound of the general formula

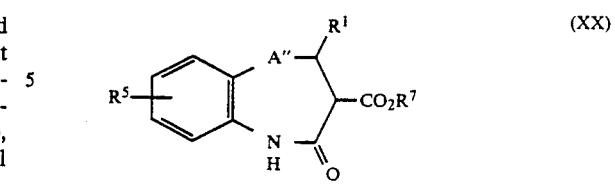

wherein each of the symbols is as defined above, by subjecting the compound of the general formula (XVI) wherein Y is amino, to ring closure reaction as mentioned above, followed by converting into the compound of the general formula

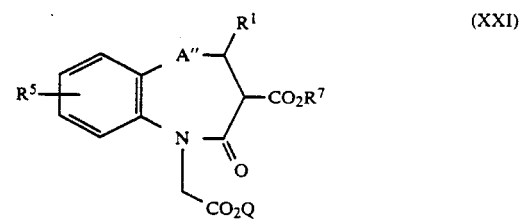

wherein each of the symbols is as defined above, by condensation reaction using the compound of the general formula (VIII) and subjecting the compound of the general formula

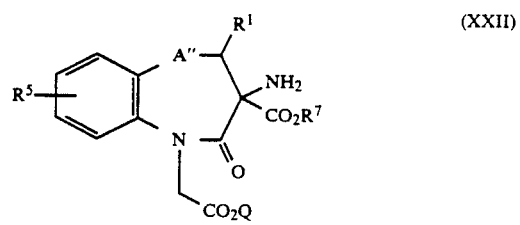

wherein each of the symbols is as defined above, which is produced by subjecting the compound (XXI) to amination reaction as described above, to the above-mentioned decarboxylation reaction.

It is needless to say that the compound of the general formula (XXII) can be produced by subjecting the compounds of the formulae (XVIII) and (VIII) to the above-mentioned condensation reaction. Additionally, the compounds (IX) and (X) can be respectively produced by converting a —CO₂R⁷ group of the compounds of the general formulae (XX) and (XXI) to amino by rearrangement reaction such as Hoffmann's rearrangement, Schmidt's rearrangement, Curtius rearrangement and so on in accordance with a known method.

Additionally, there can be mentioned the following methods for producing the compound of the general formula (I). Namely, the compound of the general formula (I) can be produced by deriving the compound of the general formula (II′) or that of the general formula (II) by the same addition-cyclization reaction as mentioned above of the compound of the general formula

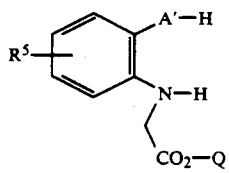

(XXIII)

wherein A', $R^5$ and Q are as defined above, which can be prepared in accordance with the method analogous to the known method with the compound of the general formula (XI), followed by conducting amidation reaction of the compound of the general formula (II') or that of the general formula (II) with the use of the compound of the general formula (III) in the same manner as mentioned above; or by deriving the compound of the general formula

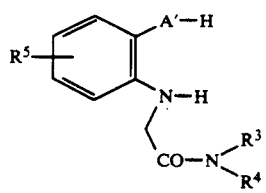

(XXIV)

wherein each of the symbols is as defined above, in advance by subjecting the compound of the general formula (XXIII) and the compound of the general formula (III) to amidation reaction, followed by subjecting the derived compound of the general formula (XIV) and the compound of the general formula (XI) to the same addition-cyclization reaction as mentioned above.

The compounds of formula (a) can be prepared, for example, by reacting the compound of formula (IX) wherein $R^1$ is $R^1a$ with the compound of formula (VIII') and then the obtained compound with the compound of formula (III). The reaction conditions are the same as mentioned above.

The separation and purification of the reaction products as obtained in the foregoing respective processes, particularly various stereoisomers, can be easily carried out by a purification method known well in the organic synthetic chemistry, which is exemplified by recrystallization, column chromatography, optical resolution and the like. The thus-obtained compounds (I) and their various isomers of the present invention can be converted to the corresponding acid addition salts by treatment with an inorganic acid (hydrochloric acid, hydrobromic acid, phosphoric acid, sulfuric acid, nitric acid, etc.) or an organic acid (maleic acid, fumaric acid, succinic acid, tartaric acid, malic acid, p-toluenesulfonic acid, etc.).

The present invention includes the following compounds which are not described in working examples.

Cis-3-[5-oxo-2(S)-pyrrolidinecarboxamido]-2-phenyl-5-(1-pyrrolidinylcarbonylmethyl)-2,3-dihydro-1,5-benzothiazepin-4(5H)-one Trans-3-[5-oxo-2(S)-pyrrolidinecarboxamido]-2-phenyl-5-(1-pyrrolidinylcarbonylmethyl)-2,3-dihydro-1,5-benzothiazepin-4(5H)-one Cis-3-[5-oxo-2(S)-pyrrolidinecarboxamido]-2-phenyl-5-piperidinocarbonylmethyl-2,3-dihydro-1,5-benzothiazepin-4(5H)-one Trans-3-[5-oxo-2(S)-pyrrolidinecarboxamido]-2-phenyl-5-piperidinocarbonylmethyl-2,3-dihydro-1,5-benzothiazepin-4(5H)-one Cis-N,N-dimethyl-4-oxo-3-[5-oxo-2(S)-pyrrolidinecarboxamido]-2-phenyl-2,3,4,5-tetrahydro-1,5-benzothiazepine-5-acetamide Trans-N,N-dimethyl-4-oxo-3-[5-oxo-2(S)-pyrrolidinecarboxamido]-2-phenyl-2,3,4,5 tetrahydro-1,5-benzothiazepine-5-acetamide Cis-N,N-diethyl-4-oxo-3-[5-oxo-2(S)-pyrrolidinecarboxamido]-2-phenyl-2,3,4,5-tetrahydro-1,5-benzothiazepine-5-acetamide Trans-N,N,-diethyl-4-oxo-3-[5-oxo-2(S)-pyrrolidinecarboxamido]-2-phenyl-2,3,4,5-tetrahydro-1,5-benzothiazepine-5-acetamide Cis-4-oxo-3-[5-oxo-2(S)-pyrrolidinecarboxamido]-N-(2-phenylethyl)-2-phenyl-2,3,4,5-tetrahydro-1,5-benzothiazepine-5-acetamide Trans-4-oxo-3-[5-oxo-2(S)-pyrrolidinecarboxamido]-N-(2-phenylethyl)-2-phenyl-2,3,4,5-tetrahydro-1,5-benzothiazepine-5-acetamide Cis-N-methyl-4-oxo-3-[5-oxo-2(S)-pyrrolidinecarboxamido]-2-phenyl-2,3,4,5-tetrahydro-1,5-benzothiazepine-5-acetamide Trans-N-methyl-4-oxo-3-[5-oxo-2(S)-pyrrolidinecarboxamido]-2-phenyl-2,3,4,5-tetrahydro-1,5-benzothiazepine-5-acetamide Cis-3-[γ-butyrolactone-γ(S)-carboxamido]-2-phenyl-5-(1-pyrrolidinylcarbonylmethyl)-2,3-dihydro-1,5-benzothiazepin-4(5H)-one Trans-3-[γ-butyrolactone-γ(S)-carboxamido]-2-phenyl-5-(1-pyrrolidinylcarbonylmethyl)-2,3-dihydro-1,5-benzothiazepin-4(5H)-one Cis-3-[γ-butyrolactone-γ(S)-carboxamido]-2-phenyl-5-piperizinocarbonylmethyl)-2,3-dihydro-1,5-benzothiazepin-4(5H)-one Trans-3-[γ-butyrolactone-γ(S)-carboxamido]-2-phenyl-5-piperizinocarbonylmethyl)-2,3-dihydro-1,5-benzothiazepin-4(5H)-one Cis-3-[γ-butyrolactone-γ(S)-carboxamido]-N,N-dimethyl-4-oxo-2-phenyl-2,3,4,5-tetrahydro-1,5-benzothiazepine-5-acetamide Trans-3-[γ-butyrolactone-γ(S)-carboxamido]-N,N-dimethyl-4-oxo-2-phenyl-2,3,4,5-tetrahydro-1,5-benzothiazepine-5-acetamide Cis-3-[γ-butyrolactone-γ(S)-carboxamido]-N,N-diethyl-4-oxo-2-phenyl-2,3,4,5-tetrahydro-1,5-benzothiazepine-5-acetamide Trans-3-[γ-butyrolactone-γ(S)-carboxamido]-N,N-diethyl-4-oxo-2-phenyl-2,3,4,5-tetrahydro-1,5-benzothiazepine-5-acetamide Cis-3-[γ-butyrolactone-γ(S)-carboxamido]-4-oxo-N-(2-phenylethyl)-2-phenyl-2,3,4,5-tetrahydro-1,5-benzothiazepine-5acetamide Trans-3-[γ-butyrolactone-γ(S)-carboxamido]-4-oxo-N-(2-phenylethyl)-2-phenyl-2,3,4,5-tetrahydro-1,5-benzothiazepine-5acetamide Cis-3-[γ-butyrolactone-γ(S)-carboxamido]-N-methyl-4-oxo-2-phenyl-2,3,4,5-tetrahydro-1,5-benzothiazepine-5-acetamide Trans-3-[γ-butyrolactone-γ(S)-carboxamido]-N-methyl-4-oxo-2-phenyl-2,3,4,5-tetrahydro-1,5-benzothiazepine-5-acetamide Cis-3-(2-indolecarboxamido)-2-phenyl-5-piperizinocarbonylmethyl)-2,3-dihydro-1,5-benzothiazepin-4(5H)-one Trans-3-(2-indolecarboxamido)-2-phenyl-5-piperizinocarbonylmethyl)-2,3-dihydro-1,5-benzothiazepin-4(5H)-one Cis-N,N-dimethyl-3-(2-indolecarboxamido)-4-oxo-2-phenyl-2,3,4,5-tetrahydro-1,5-benzothiazepine-5-acetamide Trans-N,N-dimethyl-3-(2-indolecarboxamido)-4-oxo-2-phenyl-2,3,4,5-tetrahydro-1,5-benzothiazepine-5-acetamide Cis-N,N-diethyl-3-(2-indolecarboxamido)-4-oxo-2-phenyl-2,3,4,5-tetrahydro-1,5-benzothiazepine-5-acetamide Trans-N,N-diethyl-3-(2-indolecarboxamido)-4-oxo-2-phenyl-2,3,4,5-tetrahydro-1,5-benzothiazepine-5-acetamide Cis-3-(2-cyclopentanonecarboxamido)-4-oxo-N-(2-phenylethyl)-2-phenyl-2,3,4,5-tetrahydro-1,5-benzothiazepine-5-acetamide Trans-3-(2-cyclopentanonecarboxamido)-4-oxo-N-(2-phenylethyl)-2-phenyl-2,3,4,5-tetrahydro-1,5-benzothiazepine-5-acetamide Cis-3-(2-cyclopentanonecarboxamido)-4-oxo-2-phenyl-2,3,4,5-tetrahydro-1,5-benzothiazepine-5-acetamide Trans-3-(2-cyclopentanonecarboxamido)-4-oxo-2-phenyl-2,3,4,5-tetrahydro-1,5-benzothiazepine-5-acetamide Cis-N-benzyl-4-oxo-3-[5-oxo-2(S)-pyrrolidinecarboxamido]-2-phenyl-2,3,4,5-tetrahydro-1,5-benzothiazepine-5-acetamide Trans-N-benzyl-4-oxo-3-[5-oxo-2(S)-pyrrolidinecarboxamido]-2-phenyl-2,3,4,5-tetrahydro-1,5-benzothiazepine-5-acetamide Cis-N-benzyl-3-[γ-butyrolactone-γ(S)-carboxamido]-4-oxo-2-phenyl-2,3,4,5-tetrahydro-1,5-benzothiazepine-5-acetamide Trans-N-benzyl-3-[γ-butyrolactone-γ(S)-carboxamido]-4-oxo-2-phenyl-2,3,4,5-tetrahydro-1,5-benzothiazepine-5-acetamide Cis-N-benzyl-3-(2-indolecarboxamido)-4-oxo-2-phenyl-2,3,4,5-tetrahydro-1,5-benzothiazepine-5-acetamide Trans-N-benzyl-3-(2-indolecarboxamido)-4-oxo-2-phenyl-2,3,4,5-tetrahydro-1,5-benzothiazepine-5-acetamide Cis-N-2-diphenyl-4-oxo-3-[5-oxo-2(S)-pyrrolidinecarboxamido]-2,3,4,5-tetrahydro-1,5-benzothiazepine-5-acetamide Trans-N-2-diphenyl-4-oxo-3-[5-oxo-2(S)-pyrrolidinecarboxamido]-2,3,4,5-tetrahydro-1,5-benzothiazepine-5-acetamide Cis-3-[γ-butyrolactone-γ(S)-carboxamido]-N,2-diphenyl-4-oxo-2,3,4,5-tetrahydro-1,5-benzothiazepine-5-acetamide Trans-3-[γ-butyrolactone-γ(S)-carboxamido]-N,2-diphenyl-4-oxo- 2,3,4,5-tetrahydro-1,5-benzothiazepine-5-acetamide Cis-N,2-diphenyl-3-(2-indolecarboxamido)-4-oxo-2,3,4,5-tetrahydro-1,5-benzothiazepine-5-acetamide Trans-N,2-diphenyl-3-(2-indolecarboxamido)-4-oxo-2,3,4,5-tetrahydro-1,5-benzothiazepine-5-acetamide Cis-8-chloro-3-[5-oxo-2(S)-pyrrolidinecarboxamido]-2-phenyl-5-(1-pyrrolidinylcarbonylmethyl)-2,3-dihydro-1,5-benzothiazepin-4(5H)-one Trans-8-chloro-3-[5-oxo-2(S)-pyrrolidinecarboxamido]-2-phenyl-5-(1-pyrrolidinylcarbonylmethyl)-2,3-dihydro-1,5-benzothiazepin-4(5H)-one Cis-8-chloro-3-[5-oxo-2(S)-pyrrolidinecarboxamido]-2-phenyl-5-piperidinocarbonylmethyl)-2,3-dihydro-1,5-benzothiazepin-4(5H)-one Trans-8-chloro-3-[5-oxo-2(S)-pyrrolidinecarboxamido]-2-phenyl-5-piperidinocarbonylmethyl)-2,3-dihydro-1,5-benzothiazepin-4(5H)-one Cis-8-chloro-N,N-dimethyl-4-oxo-3-[5-oxo-2(S)-pyrrolidinecarboxamido]-2-phenyl-2,3,4,5-tetrahydro-1,5-benzothiazepine-5-acetamide Trans-8-chloro-N,N-dimethyl-4-oxo-3-[5-oxo-2(S)-pyrrolidinecarboxamido]-2-phenyl-2,3,4,5-tetrahydro-1,5-benzothiazepine-5-acetamide Cis-8-chloro-N,N-diethyl-4-oxo-3-[5-oxo-2(S)-pyrrolidinecarboxamido]-2-phenyl-2,3,4,5-tetrahydro-1,5-benzothiazepine-5-acetamide Trans-8-chloro-N,N-diethyl-4-oxo-3-[5-oxo-2(S)-pyrrolidinecarboxamido]-2-phenyl-2,3,4,5-tetrahydro-1,5-benzothiazepine-5-acetamide Cis-8-chloro-4-oxo-3-[5-oxo-2(S)-pyrrolidinecarboxamido]-N-(2-phenylethyl)-2-phenyl-2,3,4,5-tetrahydro-1,5-benzothiazepine-5-acetamide Trans-8-chloro-4-oxo-3-[5-oxo-2(S)-pyrrolidinecarboxamido]-N-(2-phenylethyl)-2-phenyl-2,3,4,5-tetrahydro-1,5-benzothiazepine-5-acetamide Cis-8-chloro-N-methyl-4-oxo-3-[5-oxo-2(S)-pyrrolidinecarboxamido]-2-phenyl-2,3,4,5-tetrahydro-1,5-benzothiazepine-5-acetamide Trans-8-chloro-N-methyl-4-oxo-3-[5-oxo-2(S)-pyrrolidinecarboxamido]-2-phenyl-2,3,4,5-tetrahydro-1,5-benzothiazepine-5-acetamide Cis-3-[γ-butyrolactone-γ(S)-carboxamido]-8-chloro-2-phenyl-5-(1-pyrrolidinylcarbonylmethyl)-2,3-dihydro-1,5-benzothiazepin-4(5H)-one Trans-3-[γ-butyrolactone-γ(S)-carboxamidol-8-chloro-2-phenyl-5-(1-pyrrolidinylcarbonylmethyl)-2,3-dihydro-1,5-benzothiazepin-4(5H)-one Cis-3-[γ-butyrolactone-γ(S)-carboxamido]-8-chloro-2-phenyl-5-piperidinocarbonylmethyl)-2,3-dihydro-1,5-benzothiazepin-4(5H)-one Trans-3-[γ-butyrolactone-γ(S)-carboxamido]-8-chloro-2-phenyl-5-piperidinocarbonylmethyl)-2,3-dihydro-1,5-benzothiazepin-4(5H)-one Cis-3-[γ-butyrolactone-γ(S)-carboxamido]-8-chloro-N,N-dimethyl-4-oxo-2-phenyl-2,3,4,5-tetrahydro-1,5-benzothiazepine-5-acetamide Trans-3-[γ-butyrolactone-γ(S)-carboxamido]-8-chloro-N,N-dimethyl-4-oxo-2-phenyl-2,3,4,5-tetrahydro-1,5-benzothiazepine-5-acetamide Cis-3-[γ-butyrolactone-γ(S)-carboxamido]-8-chloro-N,N-diethyl-4-oxo-2-phenyl-2,3,4,5-tetrahydro-1,5-benzothiazepine-5-acetamide Trans-3-[γ-butyrolactone-γ(S)-carboxamido]-8-chloro-N,N-diethyl-4-oxo-2-phenyl-2,3,4,5-tetrahydro-1,5-benzothiazepine-5-acetamide Cis-3-[γ-butyrolactone-γ(S)-carboxamido]-8-chloro-4-oxo-N-(2-phenylethyl)-2-phenyl-2,3,4,5-tetrahydro-1,5-benzothiazepine-5-acetamide Trans-3-[γ-butyrolactone-γ(S)-carboxamido]-8-chloro-4-oxo-N-(2-phenylethyl)-2-phenyl-2,3,4,5-tetrahydro-1,5-benzothiazepine-5-acetamide Cis-3-[γ-butyrolactone-γ(S)-carboxamido]-8-chloro-N-methyl-4-oxo-2-phenyl-2,3,4,5-tetrahydro-1,5-benzothiazepine-5-acetamide Trans-3-[γ-butyrolactone-γ(S)-carboxamido]-8-chloro-N-methyl-4-oxo-2-phenyl-2,3,4,5-tetrahydro-1,5-benzothiazepine-5-acetamide Cis-8-chloro-3-(2-indolecarboxamido)-2-phenyl-5-piperidinocarbonylmethyl)-2,3-dihydro-1,5-benzothiazepin-4(5H)-one Trans-8-chloro-3-(2-indolecarboxamido)-2-phenyl-5-piperidinocarbonylmethyl)-2,3-dihydro-1,5-benzothiazepin-4(5H)-one Cis-8-chloro-N,N-dimethyl-3-(2-indolecarboxamido)-4-oxo-2-phenyl-2,3,4,5-tetrahydro-1,5-benzothiazepine-5-acetamide Trans-8-chloro-N,N-dimethyl-3-(2-indolecarboxamido)-4-oxo-2-phenyl-2,3,4,5-tetrahydro-1,5-benzothiazepine-5-acetamide Cis-8-chloro-N,N-diethyl-3-(2-indolecarboxamido)-4-oxo-2-phenyl-2,3,4,5-tetrahydro-1,5-benzothiazepine-5-acetamide Trans-8-chloro-N,N-diethyl-3-(2-indolecarboxamido)-4-oxo-2-phenyl-2,3,4,5-tetrahydro-1,5-benzothiazepine-5-acetamide Cis-8-chloro-3-(2-cyclopentanonecarboxamido)-4-oxo-N-(2-phenylethyl)-2-phenyl-2,3,4,5-tetrahydro-1,5-benzothiazepine-5-acetamide Trans-8-chloro-3-(2-cyclopentanonecarboxamido)-4-oxo-N-(2-phenylethyl)-2-phenyl-2,3,4,5-tetrahydro-1,5-benzothiazepine-5-acetamide Cis-8-chloro-3-(2-cyclopentanonecarboxamido)-4-oxo-2-phenyl-2,3,4,5-tetrahydro-1,5-benzothiazepine-5-acetamide Trans-8-chloro-3-(2-cyclopentanonecarboxamido)-4-oxo-2-phenyl-2,3,4,5-tetrahydro-1,5-benzothiazepine-5-acetamide Cis-N-benzyl-8-chloro-4-oxo-3-[5-oxo-2(S)-pyrrolidinecarboxamido]-2-phenyl-2,3,4,5-tetrahydro-1,5-benzothiazepine-5-acetamide Trans-N-benzyl-8-chloro-4-oxo-3-[5-oxo-2(S)-pyrrolidinecarboxamido]-2-phenyl-2,3,4,5-tetrahydro-1,5-benzothiazepine-5-acetamide Cis-N-benzyl-3-[γ-butyrolactone-γ(S)-carboxamido]-8-chloro-4-oxo-2-phenyl-2,3,4,5-tetrahydro-1,5-benzothiazepine-5-acetamide Trans-N-benzyl-3-[γ-butyrolactone-γ(S)-carboxamido]-8-chloro-4-oxo-2-phenyl-2,3,4,5-tetrahydro-1,5-benzothiazepine-5-acetamide Cis-N-benzyl-3-(2-indolecarboxamido)-8-chloro-4-oxo-2-phenyl-2,3,4,5-tetrahydro-1,5-benzothiazepine-5-acetamide Trans-N-benzyl-3-(2-indolecarboxamido)-8-chloro-4-oxo-2-phenyl-2,3,4,5-tetrahydro-1,5-benzothiazepine-5-acetamide Cis-8-chloro-N,2-diphenyl-4-oxo-3-[5-oxo-2(S)-pyrrolidinecarboxamido]-2,3,4,5-tetrahydro-1,5-benzothiazepine-5-acetamide Trans-8-chloro-N,2-diphenyl-4-oxo-3-[5-oxo-2(S)-pyrrolidinecarboxamido]-2,3,4,5-tetrahydro-1,5-benzothiazepine-5-acetamide Cis-3-[γ-butyrolactone-γ(S)-carboxamido]-8-chloro-N,2-diphenyl-4-oxo-2,3,4,5-tetrahydro-1,5-benzothiazepine-5-acetamide Trans-3-[γ-butyrolactone-γ(S)-carboxamido]-8-chloro-N,2-diphenyl-4-oxo-2,3,4,5-tetrahydro-1,5-benzothiazepine-5-acetamide Cis-8-chloro-N,2-diphenyl-3-(2-indolecarboxamido)-4-oxo-2,3,4,5-tetrahydro-1,5-benzothiazepine-5-acetamide Trans-8-chloro-N,2-diphenyl-3-(2-indolecarboxamido)-4-oxo-2,3,4,5-tetrahydro-1,5-benzothiazepine-5-acetamide Cis-3-[5-oxo-2(S)-pyrrolidinecarboxamido]-4-phenyl-1-(1-pyrrolidinylcarbonylmethyl)-1,3,4,5-tetrahydro-1-benzazepin-2(2H)-one Trans-3-[5-oxo-2(S)-pyrrolidinecarboxamido]-4-phenyl-1-(1-pyrrolidinylcarbonylmethyl)-1,3,4,5-tetrahydro-1-benzazepin-2(2H)-one Cis-3-[5-oxo-2(S)-pyrrolidinecarboxamido]-4-phenyl-1-piperidinocarbonylmethyl-1,3,4,5-tetrahydro-1-benzazepin-2(2H)-one Trans-3-[5-oxo-2(S)-pyrrolidinecarboxamido]-4-phenyl-1-piperidinocarbonylmethyl-1,3,4,5-tetrahydro-1-benzazepin-2(2H)-one Cis-N,N-dimethyl-2-oxo-3-[5-oxo-2(S)-pyrrolidinecarboxamido]-4-phenyl-2,3,4,5-tetrahydro-1H-1-benzazepine-1-acetamide Trans-N,N-dimethyl-2-oxo-3-[5-oxo-2(S)-pyrrolidinecarboxamido]-4-phenyl-2,3,4,5-tetrahydro-1H-1-benzazepine-1-acetamide Cis-N,N-diethyl-2-oxo-3-[5-oxo-2(S)-pyrrolidinecarboxamido]-4-phenyl-2,3,4,5-tetrahydro-1H-1-benzazepine-1-acetamide Trans-N,N-diethyl-2-oxo-3-[5-oxo-2(S)-pyrrolidinecarboxamido]-4-phenyl-2,3,4,5-tetrahydro-1H-1-benzazepine-1-acetamide Cis-N-methyl-2-oxo-3-[5-oxo-2(S)-pyrrolidinecarboxamido]-4-phenyl-2,3,4,5-tetrahydro-1H-1-benzazepine-1-acetamide Trans-N-methyl-2-oxo-3-[5-oxo-2(S)-pyrrolidinecarboxamido]-4-phenyl-2,3,4,5-tetrahydro-1H-1-benzazepine-1-acetamide Cis-N-benzyl-2-oxo-3-[5-oxo-2(S)-pyrrolidinecarboxamido]-4-phenyl-2,3,4,5-tetrahydro-1H-1-benzazepine-1-acetamide Trans-N-benzyl-2-oxo-3-[5-oxo-2(S)-pyrrolidinecarboxamido]-4-phenyl-2,3,4,5-tetrahydro-1H-1-benzazepine-1-acetamide Cis-2-oxo-3-[5-oxo-2(S)-pyrrolidinecarboxamido]-N-(2-phenylethyl)-4-phenyl-2,3,4,5-tetrahydro-1H-1-benzazepine-1-acetamide Trans-2-oxo-3-[5-oxo-2(S)-pyrrolidinecarboxamido]-N-(2-phenylethyl)-4-phenyl-2,3,4,5-tetrahydro-1H-1-benzazepine-1-acetamide Cis-N,4-diphenyl-2-oxo-3-[5-oxo-2(S)-pyrrolidinecarboxamido]-2,3,4,5-tetrahydro-1H-1-benzazepine-1-acetamide Trans-N,4-diphenyl-2-oxo-3-[5-oxo-2(S)-pyrrolidinecarboxamido]-2,3,4,5-tetrahydro-1H-1-benzazepine-1-acetamide Cis-3-[γ-butyrolactone-γ(S)-carboxamido]-4-phenyl-1-(1-piperidinocarbonylmethyl)-1,3,4,5-tetrahydr-1-benzazepin-2(2H)-one Trans-3-[γ-butyrolactone-γ(S)-carboxamido]-4-phenyl-1-(1-piperidinocarbonylmethyl)-1,3,4,5-tetrahydro-1-benzazepin-2(2H)-one Cis-3-[γ-butyrolactone-γ(S)-carboxamido]-4-phenyl-1-pyrrolidinylcarbonylmethyl-1,3,4,5-tetrahydro-1H-1-benzazepin-2(2H)-one Trans-3-[γ-butyrolactone-γ(S)-carboxamidol-4-phenyl-1-pyrrolidinylcarbonylmethyl-1,3,4,5-tetrahydro-1H-1-benzazepin-2(2H)-one Cis-3-[γ-butyrolactone-γ(S)-carboxamido]-N,N-dimethyl-2-oxo-4-phenyl-2,3,4,5-tetrahydro-1H-1-benzazepine-1-acetamide Trans-3-[γ-butyrolactone-γ(S)-carboxamido]-N,N-dimethyl-2-oxo-4-phenyl-2,3,4,5-tetrahydro-1H-1-benzazepine-1-acetamide Cis-3-[γ-butyrolactone-γ(S)-carboxamido]-N,N-diethyl-2-oxo-4-phenyl-2,3,4,5-tetrahydro-1H-1-benzazepine-1-acetamide Trans-3-[γ-butyrolactone-γ(S)-carboxamido]-N,N-diethyl-2-oxo-4-phenyl-2,3,4,5-tetrahydro-1H-1-benzazepine-1-acetamide Cis-3-[γ-butyrolactone-γ(S)-carboxamido]-N-methyl-2-oxo-4-phenyl-2,3,4,5-tetrahydro-1H-1-benzazepine-1-acetamide Trans-3-[γ-butyrolactone-γ(S)-carboxamido]-N-methyl-2-oxo-4-phenyl-2,3,4,5-tetrahydro-1H-1-benzazepine-1-acetamide Cis-N-benzyl-3-[γ-butyrolactone-γ(S)-carboxamido]-2-oxo-4-phenyl-2,3,4,5-tetrahydro-1H-1-benzazepine-1-acetamide Trans-N-benzyl-3-[γ-butyrolactone-γ(S)-carboxamido]-2-oxo-4-phenyl-2,3,4,5-tetrahydro-1H-1-benzazepine-1-acetamide Cis-3-[γ-butyrolactone-γ(S)-carboxamido]-2-oxo-N-(2-phenylethyl)-4-phenyl-2,3,4,5-tetrahydro-1H-1-benzazepine-1-acetamide Trans-3-[γ-butyrolactone-γ(S)-carboxamido]-2-oxo-N-(2-phenylethyl)-4-phenyl-2,3,4,5-tetrahydro-1H-1-benzazepine-1-acetamide Cis-3-[γ-butyrolactone-γ(S)-carboxamido]-N,4-diphenyl-2-oxo-2,3,4,5-tetrahydro-1H-1-benzazepine-1-acetamide Trans-3-[γ-butyrolactone-γ(S)-carboxamido]-N,4-diphenyl-2-oxo-2,3,4,5-tetrahydro-1H-1-benzazepine-1-acetamide Cis-3-(2-indolecarboxamido)-2-oxo-N-(2-phenylethyl)-4-phenyl-2,3,4,5-tetrahydro-1H-1-benzazepine-1-acetamide Trans-3-(2-indolecarboxamido)-2-oxo-N-(2-phenylethyl)-4-phenyl-2,3,4,5-tetrahydro-1H-1-benzazepine-1-acetamide Trans-3-(2-indolecarboxamido)-2-oxo-4-phenyl-2,3,4,5-tetrahydro-1H-1,5-benzodiazepine-1-acetamide Cis-3-(2-indolecarboxamido)-2-oxo-4-phenyl-2,3,4,5-tetrahydro-1H-1,5-benzodiazepine-1-acetamide Trans-3-[γ-butyrolactone-γ(S)-carboxamido]-2-oxo-4-phenyl-2,3,4,5-tetrahydro-1H-1,5-benzodiazepine-1-acetamide Cis-3-[γ-butyrolactone-γ(S)-carboxamido]-2-oxo-4-phenyl-2,3,4,5-tetrahydro-1H-1,5-benzodiazepine-1-acetamide Trans-2-oxo-3-[5-oxo-2(S)-pyrrolidinecarboxamido]-4-phenyl-2,3,4,5-tetrahydro-1H-1,5-benzodiazepine-1-acetamide Cis-2-oxo-3-[5-oxo-2(S)-pyrrolidinecarboxamido]-4-phenyl-2,3,4,5-tetrahydro-1H-1,5-benzodiazepine-1-acetamide Trans-3-(2-indolecarboxamido)-5-methyl-2-oxo-4-phenyl-2,3,4,5-tetrahydro-1H-1,5-benzodiazepine-1-acetamide Cis-3-(2-indolecarboxamido)-5-methyl-2-oxo-4-phenyl-2,3,4,5-tetrahydro-1H-1,5-benzodiazepine-1-acetamide Trans-3-[γ-butyrolactone-γ(S)-carboxamido]-5-methyl-2-oxo-4-phenyl-2,3,4,5-tetrahydro-1H-1,5-benzodiazepine-1-acetamide Cis-3-[γ-butyrolactone-γ(S)-carboxamido]-5-methyl-2-oxo-4-phenyl-2,3,4,5-tetrahydro-1H-1,5-benzodiazepine-1-acetamide Trans-5-methyl-2-oxo-3-[5-oxo-2(S)-pyrrolidinecarboxamido]-4-phenyl-2,3,4,5-tetrahydro-1H-1,5-benzodiazepine-1-acetamide Cis-5-methyl-2-oxo-3-[5-oxo-2(S)-pyrrolidinecarboxamido]-4-phenyl-2,3,4,5-tetrahydro-1H-1,5-benzodiazepine-1-acetamide Trans-3-(2-indolecarboxamido)-4-phenyl-1-(2-phenylethylaminocarbonylmethyl)-1,3,4,5-tetrahydro-1,5-benzodiazepin-2(2H)-one Cis-3-(2-indolecarboxamido)-4-phenyl-1-(2-phenylethylaminocarbonylmethyl)-1,3,4,5-tetrahydro-1,5-benzodiazepin-2(2H)-one Trans-3-[γ-butyrolactone-γ(S)-carboxamido]-4-phenyl-1-(2-phenylethylaminocarbonylmethyl)-1,3,4,5-tetrahydro-1,5-benzodiazepin-2(2H)-one Cis-3-[γ-butyrolactone-γ(S)-carboxamido]-4-phenyl-1-(2-phenylethylaminocarbonylmethyl)- 1,3,4,5-tetrahydro-1,5-benzodiazepin-2(2H)-one Trans-3-[5-oxo-2(S)-pyrrolidinecarboxamido]-4-phenyl-1-(2-phenylethylaminocarbonylmethyl)-1,3,4,5-tetrahydro-1,5-benzodiazepin-2(2H)-one Cis-3-[5-oxo-2(S)-pyrrolidinecarboxamido]-4-phenyl-1-(2-phenylethylaminocarbonylmethyl)-1,3,4,5-tetrahydro-1,5-benzodiazepin-2(2H)-one Trans-3-(2-indolecarboxamido)-5-methyl-4-phenyl-1-(2-phenylethylaminocarbonylmethyl)-1,3,4,5-tetrahydro-1,5-benzodiazepin-2(2H)-one Cis-3-(2-indolecarboxamido)-5-methyl-4-phenyl-1-(2-phenyl-ethylaminocarbonylmethyl)-1,3,4,5-tetrahydro-1,5-benzodiazepin-2(2H)-one Trans-3-[γ-butyrolactone-γ(S)-carboxamido]-5-methyl-4-phenyl-1-(2-phenylethylaminocarbonylmethyl)-1,3,4,5-tetrahydro-1,5-benzodiazepin-2(2H)-one Cis-3-[γ-butyrolactone-γ(S)-carboxamido]-5-methyl-4-phenyl-1-(2-phenylethylaminocarbonylmethyl)-1,3,4,5-tetrahydro-1,5-benzodiazepin-2(2H)-one Trans-5-methyl-3-[5-oxo-2(S)-pyrrolidinecarboxamido]-4-phenyl-1-(2-phenylethylaminocarbonylmethyl)-1,3,4,5-tetrahydro-1,5-benzodiazepin-2(2H)-one Cis-5-methyl-3-[5-oxo-2(S)-pyrrolidinecarboxamido]-4-phenyl-1-(2-phenylethylaminocarbonylmethyl)-1,3,4,5-tetrahydro-1,5-benzodiazepin-2(2H)-one 2-Benzyl-3-[γ-butyrolactone-γ(S)-carboxamido]-4-oxo-2,3,4,5-tetrahydro-1,5-benzothiazepine-5-acetamide;

3-[γ-Butyrolactone-γ(S)-carboxamido]-N,N-dimethyl-4-oxo-2-phenyl-2,3,4,5-tetrahydro-1,5-benzothiazepine-5-acetamide;

N,N-Dimethyl-3-(2-indolecarboxamido)-4-oxo-2-phenyl-2,3,4,5-tetrahydro-1,5-benzothiazepine-5-acetamide;

3-[γ-Butyrolactone-γ(S)-carboxamido]-2-isopropyl-4-oxo-2,3,4,5-tetrahydro-1,5-benzothiazepine-5-acetamide;

2-Isopropyl-4-oxo-3-[5-oxo-2(S)-pyrrolidinecarboxamido]-2,3,4,5-tetrahydro-1,5-benzothiazepine-5-acetamide;

2-Isopropyl-4-oxo-3-[2(S)-pyrrolidinecarboxamido]-2,3,4,5-tetrahydro-1,5-benzothiazepine-5-acetamide;

3-[γ-Butyrolactone-γ(S)-carboxamido]-4-oxo-2-(3-pyridyl)-2,3,4,5-tetrahydro-1,5-benzothiazepine-5-acetamide;

3-(2-Indolecarboxamido)-4-oxo-2-(3-pyridyl)-2,3,4,5-tetrahydro-1,5-benzothiazepine-5-acetamide;

3-(1-Methyl-4,5-dihydroorotyl)amino-4-oxo-2-phenyl-2,3,4,5-tetrahydro-1,5-benzothiazepine-5-acetamide;

3-(1-Methyl-4,5-dihydroorotyl)amino-4-oxo-2-(2-thienyl)-2,3,4,5-tetrahydro-1,5-benzothiazepine-5-acetamide;

3-[γ-Butyrolactone-γ(S)-carboxamido]-8-chloro-4-oxo-2-phenyl-2,3,4,5-tetrahydro-1,5-benzothiazepine-5-acetamide;

3-[γ-Butyrolactone-γ(S)-carboxamido]-8-methyl-4-oxo-2-phenyl-2,3,4,5-tetrahydro-1,5-benzothiazepine-5-acetamide;

3-[γ-Butyrolactone-γ(S)-carboxamido]-8-methoxy-4-oxo-2-phenyl-2,3,4,5 tetrahydro-1,5-benzothiazepine-5-acetamide;

2-(5-Bromo-2-thienyl)-3-[γ-butyrolactone-γ(S)-carboxamido]-4-oxo-2,3,4,5-tetrahydro-1,5-benzothiazepine-5-acetamide;

3-[γ-Butyrolactone-γ(S)-carboxamido]-2-(5-methyl-2-thienyl)-4-oxo-2,3,4,5-tetrahydro-1,5-benzothiazepine-5-acetamide;

3-[γ-Butyrolactone-γ(S)-carboxamido]-2-(3-methyl-2-thienyl)-4-oxo-2,3,4,5-tetrahydro-1,5-benzothiazepine-5-acetamide;

2-(5-Bromo-2-thienyl)-3-(2-indolecarboxamido)-4-oxo-2,3,4,5-tetrahydro-1,5-benzothiazepine-5-acetamide;

3-[γ-Butyrolactone-γ(S)-carboxamido]-2-(4-imidazolyl)-4-oxo-2,3,4,5-tetrahydro-1,5-benzothiazepine-5-acetamide;

2-(4-Imidazolyl)-4-oxo-3-[5-oxo-2(S)-pyrrolidinecarboxamido]-2,3,4,5-tetrahydro-1,5-benzothiazepine-5-acetamide;

2-(4-Imidazolyl)-3-(2-indolecarboxamido)-4-oxo-2,3,4,5-tetrahydro-1,5-benzothiazepine-5-acetamide;

2-(2-Aminothiazol-4-yl)3-[γ-butyrolactone-γ(S)-carboxamido]-4-oxo-2,3,4,5-tetrahydro-1,5-benzothiazepine-5-acetamide;

2-(2-Aminothiazol-4-yl)-4-oxo-3-[5-oxo-2(S)-pyrrolidinecarboxamido]-2,3,4,5-tetrahydro-1,5-benzothiazepine-5-acetamide;

2-(2 Aminothiazol-4-yl)-3-(2-indolecarboxamido)-4-oxo-2,3,4,5-tetrahydro-1,5-benzothiazepine-5-acetamide;

3-[γ-Butyrolactone-γ(S)-carboxamido]-4-oxo-2-phenyl-2,3,4,5-tetrahydro-1,5-benzoxepine-5-acetamide;

3-(2-Indolecarboxamido)-4-oxo-2-phenyl-2,3,4,5-tetrahydro-1,5-benzoxepine-5-acetamide;

3-[γ-Butyrolactone-γ(S)-carboxamido]-2-oxo-4-phenyl-2,3,4,5-tetrahydro-1H -1,5-benzodiazepine-1-acetamide;

3-(2-Indolecarboxamido)-2-oxo-4-phenyl-2,3,4,5-tetrahydro-1H-1,5-benzodiazepine-1-acetamide;

3-(γ-Butyrolactone-γ(S)-carboxamido]-2-oxo-4-phenyl-2,3,4,5-tetrahydro-1H-1-benzazepine-1-acetamide;

3-(2-Indolecarboxamido)-2-oxo-4-phenyl-2,3,4,5-tetrahydro-1H-1-benzazepine-1-acetamide;

3-[γ-Butyrolactone-γ(S)-carboxamido]-2,5-dioxo-4-phenyl-2,3,4,5-tetrahydro-1H-1-benzazepine-1-acetamide;

3-(2-Indolecarboxamido)-2,5-dioxo-4-phenyl-2,3,4,5-tetrahydro-1H-1-benzazepine-1-acetamide.

As one of the methods for evaluating improving actions for consciousness disturbance, remembrance disturbance or dementia caused by brain function disturbance or brain organ disturbance, various experimentally amnesia-induced models have been used [Japanese Journal of Psychopharmacology, vol. 3, p. 127 (1983); ibid., vol. 5, P. 1 (1985); Japanese Journal of Pharmacology, vol. 39, p. 153 (1985), Psychopharmacology, vol. 78, p. 104 (1982), etc.].

The benzolactam compounds of the present invention exhibit an improving action on the above-mentioned experimental amnesia induced by electro convulsive shock and elongate survival time under hypoxic condition. Further, they exhibit a strong effect even when orally administered and they are low in toxicity and excellent in duration of their effect. Thus, the benzolactam compounds of the present invention are useful as a brain function-improving and brain function-treating agent.

Pharmacological Experiment: Effects on Experimental Amnesia

The experiment was conducted in accordance with the method by Sara et al. as described in Psychopharmacologia vol. 36, p. 59 (1974).

Male ddY mice weighing 23-26 g, 20 animals per group, were used, and a practicing apparatus for step-through passive avoidance response was used. As the acquisition trial, an animal was placed into the lighted compartment, and as soon as the animal entered the dark compartment, the animal received foot shock. Experimental amnesia was induced by exposing electroconvulsive shock (ECS) immediately after the acquisition trial. As the test trial, the animal was placed into the lighted compartment three hours after the acquisition trial, and the time (latency) which the animal took to enter the dark compartment was measured up to 600 seconds at maximum. The test compound was intraperitoneally administered immediately after exposure to ECS.

For the evaluation of the effect, the antagonistic action on shortening of latency induced by exposure to ECS was examined. The minimum effective dose of the test compound that shows a significant antagonistic action as compared with the controls is shown in Table 1.

TABLE 1

| Test Compound (Example No.) | Antiamnesic Action Minimum Effective Dose (mg/kg i.p.) |
| --- | --- |
| 1 (A Isomer) | 1 |
| 1 (B Isomer) | 0.25 |
| 2 | 0.25 |
| 3 (B Isomer) | 0.5 |
| 4 | 0.5 |
| 5 | 0.5 |
| 8 | 0.5 |
| 10 | 0.5 |
| 11 (B Isomer) | 1 |
| 12 | 0.5 |
| 14 | 0.5 |
| 16 | 0.5 |
| 19 (A Isomer) | 2.5 |
| 19 (B Isomer) | 0.25 |
| 23 (B Isomer) | 2.5 |
| 24 (A Isomer) | 2.5 |
| 35 | 0.25 |
| 36 (B Isomer) | 0.2 |

Pharmacological Experiment 2: Effect on Stress Ulcer

Female Wistar rats, 5 animals per group, was fasted for 20 hours, and then administered orally with test compound solution. After 30 minutes, the rats were placed into a stress cage and immersed to the level of xiphoid in a water bath at $23\pm2°$ C. for 6 hours. The animals were then sacrificed and to the isolated stomachs were poured 8 ml of 1% formalin solution. After ligation, the stamachs were immersed in the formalin solution and fixed and then opened.

The compound of Example 1(v) show 25% inhibition against stress ulcer at an oral dose of 30 mg/kg.

Pharmacological Experiment 3: Effect on Urine Volume

Female ddY mice, 2 animals per group, were used. After fasting and depriving of water for 21 hours, the mice was orally administered with test compound suspended in a 0.9% saline solution and put into an apparatus for collecting urine in which a filter paper was laid.

The urine excreted within 2 hours after the administration, was adsorbed in the filter paper and the urine weight was assayed with comparing with the control group.

The compound of Example 23(iv) show 60% increase of the urine volume comparing to the control group at an oral dose of 100 mg/kg.

When the compounds of the present invention are used as pharmaceuticals, they are orally or parenterally administered as they are or in a form of dispersible powders, granules, tablets, capsules or injectable compositions adequately in admixture with pharmacologically acceptable carriers, excipients, diluents and so on. While the dosage varies depending upon the target disease, symptom, the compounds to be used, the general daily dosage is in the range of about 1 to 500 mg per adult in the case of oral administration.

FORMULATION EXAMPLE

In case the compound of the present invention is used as a brain function-improving drug, the drug is prepared, for example, in accordance with the following composition.

| (a) Tablets | |
| --- | --- |
| The compound of the present invention | 30 mg |
| Lactose | 150 mg |
| Crystalline cellulose | 50 mg |
| Carboxymethyl cellulose Calcium | 7 mg |
| Magnesium stearate | 3 mg |
| Total | 240 mg |

The instant tablets may be subjected to conventional film-coating, and additionally to sugar-coating.

| (b) Granules | |
| --- | --- |
| The compound of the present invention | 30 mg |
| Polyvinylpyrrolidone | 25 mg |
| Lactose | 385 mg |
| Hydroxypropyl cellulose | 50 mg |
| Talc | 10 mg |
| Total | 500 mg |
| (c) Dispersible Powders | |
| The compound of the present invention | 30 mg |
| Lactose | 300 mg |
| starch | 440 mg |
| Colloidal silica | 30 mg |
| Total | 1000 mg |
| (d) Capsules | |
| The compound of the present invention | 30 mg |
| Lactose | 102 mg |
| Crystalline cellulose | 56 mg |
| Colloidal silica | 2 mg |
| Total | 190 mg |

(e) Injectable Preparation

An aqueous solution containing the compound of the present invention in an amount of 1 to 30 mg per 1 ml of the aqueous solution (pH 6.5-7.0) is prepared under aseptic conditions.

Hereafter, the present invention is in further detail explained by illustrating working examples, which are by no means to be interpreted as limitative. In the examples, CDCl$_3$ represents deutrochloroform, DMSO stands for dimethyl sulfoxide, DMSO-d$_6$ stands for deutrodimethyl sulfoxide and KBr represents potassium bromide.

EXAMPLE 1

(i) In 140 ml of ethanol are dissolved 30.6 g of o-aminobenzenethiol and 66 g of N-benzyloxycarbonyl-α-dehydro-β-phenylalanine, and the solution is stirred under reflux for 24 hours. After the completion of the reaction, the resulting mixture is cooled at room temperature. The separated crystals are filtered to give 57 g of N-benzyloxycarbonyl-S-(2-aminophenyl)-β-phenylcysteine.

(ii) N-benzyloxycarbonyl-S-(2-aminophenyl)-β-phenylcysteine (155 g) is admixed with 3.6 l of xylene, and the mixture is stirred under reflux with water being removed for 4.5 hours. After cooling at room temperature, the separated crystals are collected by filtration to give 52.5 g of trans-3-benzyloxycarboxamido-2-phenyl-2,3-dihydro-1,5-benzothiazepin-4(5H)-one, m.p. 235°-237° C.

The filtrate is concentrated under reduced pressure to the volume of about 1 l, and the resulting crystals are collected by filtration. The obtained crystals are separated, purified by way of silica gel column chromatography (elute:chloroform:methanol=20:1) and recrystallized from isopropyl alcohol to give 3 g of cis-3-benzyloxycarboxamido-2-phenyl-2,3-dihydro-1,5-benzothiazepin-4(5H)-one, m:p. 186°-189° C.

(iii) To a mixture of 69.5 g of trans-3-benzyloxycarboxamido-2-phenyl-2,3-dihydro-1,5-benzothiazepin-4(5H)-one, 18 ml of anisole and 40 ml of acetic acid is added 300 ml of 30% hydrogen bromide-acetic acid, and the mixture is stirred at room temperature for 1.5 hours. After the completion of the reaction, a mixed solvent of 1 l of ether and 0.5 l of isopropyl ether is added thereto, and the resulting crystals are collected by filtration. After thus obtained crystals are washed with ether, they are added to a mixture of 1 l of a 10% aqueous solution of sodium carbonate and 3 l of chloroform. The precipitated organic substance is extracted. The chloroform layer is washed with water, dried over magnesium sulfate and concentrated under reduced pressure. The residue is recrystallized from isopropyl alcohol to give 41.5 g of trans-3-amino-2-phenyl-2,3-dihydro-1,5-benzothiazepin-4(5H)-one, m.p. 218°-221° C. The melting point of the hydrobromide: 272°-293° C. (decomposition).

NMR spectrum of the hydrobromide [DMSO-d$_6$, tetramethylsilane (TMS) as inner standard (ppm)]:

δ=4.27 (d, 1H, J=12Hz), 4.78 (d, 1H, J=12Hz), 7.1-7.8 (9H), 10.73 (s, 1H).

(iv) In 700 ml of dimethylformamide is dissolved 54.8 g of trans-3-amino-2-phenyl-2,3-dihydro-1,5-benzothiazepin-4(5H)-one. To this solution is added 8.8 g of 60% sodium hydride under ice-cooling. The reaction temperature is gradually elevated to room temperature, and the mixture is stirred for 1.5 hours. After the reaction mixture is again cooled to about 10° C., 100 ml of a dimethylformamide solution containing 25.5 ml of ethyl bromoacetate is added dropwise. After the reaction temperature is elevated again to room temperature, the mixture is stirred for 5 hours and then concentrated under reduced pressure. By adding ice-water and chloroform to the residue, the organic substance is extracted. After the chloroform layer is washed with water and dried, the solvent is distilled off under reduced pressure. By adding a mixed solution of isopropyl ether and isopropyl alcohol to the residue, the crystallization is effected. The resulting crystals are collected by filtration to give 37 g of ethyl trans-3-amino-4-oxo-2- phenyl-2,3,4,5-tetrahydro-1,5-benzothiazepine-5-acetate.

NMR spectrum (CDCl$_3$; ppm): δ=1.31 (t, 3H), 1.58 (brs, 2H), 3.7–4.4 (5H), 4.93 (d, 1H, J=17Hz), 6.9–7.7 (9H).

(v) In 600 ml of methanol is dissolved 20 g of ethyl trans-3-amino-4-oxo-2-phenyl-2,3,4,5-tetrahydro-1,5-benzothiazepine-5-acetate, into which ammonia gas is blown to the level of saturation under ice-cooling. The reaction temperature is slowly elevated to room temperature, and the mixture is allowed to stand still for 24 hours. Then, the reaction mixture is concentrated under reduced pressure. By adding isopropyl alcohol to the obtained residue, crystallization is effected. The crystals are collected by filtration to give 18 g of trans-3-amino-4-oxo-2-phenyl-2,3,4,5-tetrahydro-1,5-benzothiazepine-5-acetamide, m.p. 217°–219° C.

NMR spectrum (CDCl$_3$; ppm): δ=1.68 (brs, 2H), 3.83 (d, 1H, J=10Hz), 4.19 (d, 1H, J=10Hz), 4.4 (d, 1H, J=16Hz), 4.74 (d, 1H, J=16Hz), 6.8–7.8 (9H).

(vi) With 100 ml of dichloromethane are mixed 3.2 g of succinimido γ-butyrolactone-γ(S)-carboxylate as obtained in accordance with a method analogous to the known method and 3.2 g of trans-3-amino-4-oxo-2-phenyl-2,3,4,5-tetrahydro-1,5-benzothiazepine-5-acetamide. While the mixture is stirred at room temperature for 8.5 hours, the reaction mixture gradually comes to dissolve. After the reaction mixture is allowed to stand overnight, a 5% aqueous solution of sodium hydrogencarbonate is added thereto and the mixture is stirred for a while to yield crystals. The crude crystals are collected by filtration and recrystallized from methanol to give 1.1 g of trans-3(S)-[γ-butyrolactone-γ(S)-carboxamido]-4-oxo-2(R)-phenyl-2,3,4,5-tetrahydro-1,5-benzothiazepine-5-acetamide (A isomer). Meanwhile, the organic layer separated from the filtrate by addition of chloroform is washed with a saturated aqueous solution of sodium hydrogencarbonate and then with water, and dried over magnesium sulfate. After the solvent is distilled off under reduced pressure, isopropyl alcohol is added to the residue to yield crystals, which are recrystallized from ethanol to give 1.7 g of trans-3(R)-[γ-butyrolactone-γ(S)-carboxamido]-4-oxo-2(S)-phenyl-2,3,4,5-tetrahydro-1,5-benzothiazepine-5-acetamide (B isomer).

A isomer: m.p. 264°–267° C.

$^{13}$C NMR spectrum (DMSO-d$_6$; TMS as inner standard, ppm): δ=25.6, 26.2, 51.6, 52.7, 54.4, 75.6, 124.2, 124.9, 127.5, 126.8, 128.0, 131.3, 135.6, 141, 145.7, 168.5, 169.2, 176.5.

[α]$_D$= +565° (c=0.5%, DMSO).

B isomer: m.p. 248°–250° C.

$^{13}$C NMR spectrum (DMSO-d$_6$; ppm): δ=25.2, 26.4, 51.7, 53.0, 53.8, 76.1, 124.2, 124.9, 126.8, 127.5, 128.0, 131.3, 135.7, 141.1, 145.6, 168.7, 169.3, 1.76.3.

[α]$_D$= −502° (c=0.5%, DMSO)

EXAMPLE 2

(i) To a mixture of 4.7 g of cis-3-benzyloxycarboxamido-2-phenyl-2,3-dihydro-1,5-benzothiazepin-4(5H)-one which is obtained in (ii) of Example 1, 2.5 ml of acetic acid and 1.3 ml of anisole is added 20 ml of 30%-hydrogen bromide-acetic acid in the same manner as in (iii) of Example 1, and the mixture is stirred at room temperature for 1 hour. After the completion of the reaction, 150 ml of isopropyl ether is added, followed by decantation. The obtained oily residue is crystallized from ether. The crystals collected by filtration are washed with isopropyl ether and dried under reduced pressure to give 3.5 g of cis-3-amino-2-phenyl-2,3-dihydro-1,5-benzothiazepin-4(5H)-one hydrobromide, m.p. 253°–258° C.

NMR spectrum (DMSO-d$_6$; ppm): δ=4.25 (d, 1H, J=7Hz), 5.29 (d, 1H, J=7Hz), 7.1–7.9 (9H).

(ii) With 40 ml of dimethylformamide is mixed 3 g of cis-3-amino-2-phenyl-2,3-dihydro-1,5-benzothiazepin-4(5H)- one hydrobromide in the same manner as in (iv) of Example 1, and 0.72 g of 60% sodium hydride is added to the mixture under ice-cooling. After the temperature is gradually elevated to room temperature, the mixture is stirred for 2 hours. After the temperature of the reaction mixture is again cooled to about 10° C., 5 ml of a dimethylformamide solution containing 1.1 ml of ethyl bromoacetate is added dropwise thereto. Then, the reaction temperature is elevated to room temperature, and the reaction mixture is stirred for 6 hours, followed by concentration under reduced pressure. By adding ice water and chloroform to the residue, the organic substance is extracted. The chloroform layer is washed with water and dried. Thereafter, the solvent is distilled off under reduced pressure. The purification of the obtained residue by silica gel chromatography gives 3.0 g of ethyl cis-3-amino-4-oxo-2-phenyl-2,3,4,5-tetrahydro-1,5-benzothiazepine-5-acetate as oily substance.

NMR spectrum (CDCl$_3$; ppm): δ=1.31 (t, 3H), 1.58 (brs, 2H), 3.8–5.1 (6H), 7.1–7.8 (9H).

(iii) With the use of 3.0 g of ethyl cis-3-amino-4-oxo-2-phenyl-2,3,4,5-tetrahydro-1,5-benzothiazepine-5-acetate, the same reaction procedure as in (v) of Example 1 is carried out to give 1.8 g of cis-3-amino-4-oxo-2-phenyl-2,3,4,5-tetrahydro-1,5-benzothiazepine-5-acetamide, m.p. 196°–200° C.

NMR spectrum (CDCl$_3$; ppm): δ=1.44 (brs, 2H), 3.87 (d, 1H, J=8Hz), 4.44 (d, 1H, J=16Hz), 4.84 (d, 1H, J=16Hz), 4.89 (d, 1H, J=8Hz), 6.9–8.0 (10H), 6.05 (brs, 1H)

(iv) In the same manner as in (vi) of Example 1, 1.3 g of succinimido γ-butyrolactone-γ(S)-carboxylate and 1.13 g of cis-3-amino-4-oxo-2-phenyl-2,3,4,5-tetrahydro-1,5-benzothiazepine-5-acetamide are mixed with 30 ml of dichloromethane, and the mixture is stirred at room temperature for 25 hours. After a 5% aqueous solution of sodium hydrogencarbonate is added to the reaction mixture, the mixture is stirred for a while, and then chloroform is added thereto to separate the organic layer. The organic layer is washed with water, dried and concentrated under reduced pressure. The obtained residue is recrystallized from isopropyl alcohol to give 0.9 g of ½ isopropyl alcohol solvate of cis-3-[γ-butyrolactone-γ(S)-carboxamido]-4-oxo-2-phenyl-2,3,4,5-tetrahydro-1,5-benzothiazepine-5-acetamide, m.p. 143°–146° C. [α]$_D$= +20° (c=0.1%, DMSO)

EXAMPLE 3

In 70 ml of dimethylformamide are dissolved 3.27 g of trans-3-amino-4-oxo-2-phenyl-2,3,4,5-tetrahydro-1,5-benzothiazepine-5-acetamide as obtained in (v) of Example 1 and 1.29 g of L-pyroglutamic acid, whereto 2.06 g of dicyclohexylcarbodiimide is added. The mixture is stirred at room temperature for 8 hours. The separated crystals are removed by filtration, and the filtrate is concentrated under reduced pressure. Chloroform is added to the concentrated residue. The organic layer is washed with a diluted aqueous hydrochloric acid and water, and dried over magnesium sulfate. The solvent is distilled off under reduced pressure. Isopropyl alcohol is added to the obtained residue to yield crystals. The crude crystals collected by filtration is recrystallized from methanol to give 0.9 g of B isomer of trans-4-oxo-3-[5-oxo-2(S)-pyrrolidinecarboxamido]-2-phenyl-2,3,4,5-tetrahydro-1,5-benzothiazepine-5-acetamide as the monohydrate. On the other hand, the mother liquor of the recrystallization from methanol is concentrated under reduced pressure, and the residue is purified by silica gel chromatography. The elute is concentrated under reduced pressure, and the obtained solid residue is recrystallized from isopropyl alcohol to give 0.38 g of A isomer of trans-4-oxo-3-[5-oxo-2(S)-pyrrolidinecarboxamido]-2-phenyl-2,3,4,5-tetrahydro-1,5-benzothiazepine-5-acetamide as ½ isopropyl alcohol solvate.

A isomer (as ½ isopropyl alcohol solvate): m.p. 189°–199° C.

NMR spectrum (DMSO-$d_6$; ppm): $\delta = 3.5$–$4.2$ (2H), $4.4$–$5.1$ (3H), $6.9$–$7.7$ (11H), $8.57$ (d, 1H).

$[\alpha]_D = +520°$ (c=0.1%, DMSO)

B isomer (as monohydrate): m.p. 199°–204° C.

NMR spectrum (DMSO-$d_6$; ppm): $\delta = 1.1$–$2.2$ (4H), $3.5$–$5.1$ (5H), $6.9$–$7.8$ (11H), $8.43$ (d, 1H).

$[\alpha]_D = -507°$ (c=0.1%, DMSO).

EXAMPLE 4

With 80 ml of dichloromethane are mixed 2.0 g of trans-3-amino-4-oxo-2-phenyl-2,3,4,5-tetrahydro-1,5-benzothiazepine-5-acetamide as obtained in (v) of Example 1, 1.0 g of 2-indolecarboxylic acid and 1.87 g of 2-chloro-N-methylpyridinium iodide, whereto 3.5 ml of tri-n-butylamine is added while stirring at room temperature. The reaction mixture once dissolves, and then the crystals separate again. After stirring for 2 hours, the crystals are removed by filtration, and chloroform and water are added to the filtrate. The separated organic layer is washed with a 10% aqueous solution of hydrochloric acid, aqueous sodium chloride, an aqueous solution of potassium carbonate and saline in order, and dried over magnesium sulfate. The solvent is distilled off under reduced pressure, and isopropyl ether is added to the residue to crystallize. The resulting crystals are collected by filtration to give 0.95 g of trans-3-(2-indolecarboxamido)-4-oxo-2-phenyl-2,3,4,5-tetrahydro-1,5-benzothiazepine-5-acetamide, m.p. 222°–225° C.

NMR spectrum (DMSO-$d_6$; ppm): $\delta = 3.9$–$5.2$ (4H), $6.8$–$7.8$ (16H), $8.86$ (d, 1H).

EXAMPLE 5

With 30 ml of dimethylformamide are mixed 1.65 g of 4,5-dihydroorotic acid prepared by the known method, 1.27 g of N-hydroxysuccinimide and 2.27 g of dicyclohexylcarbodiimide, and the mixture is stirred at room temperature overnight. To the filtrate obtained by removing the separated crystals by filtration, 3.27 g of trans-3-amino-4-oxo-2-phenyl-2,3,4,5-tetrahydro-1,5-benzothiazepine-5-acetamide which is obtained in (v) of Example 1 is added under ice-cooling. The mixture is stirred for 6.5 hours while the reaction temperature is slowly elevated to room temperature. After the resulting insoluble substances are removed by filtration, the filtrate is concentrated under reduced pressure. Water is added to the residue to yield crystals. The crude crystals collected by filtration are recrystallized from a mixed solvent of dimethylformamide and methanol to give 4.1 g of trans-3-(4,5-dihydroorotylamino)-4-oxo-2-phenyl-2,3,4,5-tetrahydro-1,5-benzothiazepine-5-acetamide hemihydrate, m.p. 268°–272°C. (decomposition).

$[\alpha]_D = +45°$ (c=1%, DMSO).

EXAMPLE 6

By following the same reaction procedure as in Example 5 using 1.7 g of 5-oxo-3-carboxyperhydro-1,4-thiazine instead of 4,5-dihydroorotic acid, 1.5 g of trans-4-oxo-3-(5-oxoperhydro-1,4-thiazine-3-carboxamido)-2-phenyl-2,3,4,5-tetrahydro1,5-benzothiazepine-5-acetamide monohydrate is obtained, m.p. 259°–262° C. (decomposition).

EXAMPLE 7

With 30 ml of pyridine are mixed 2.29 g of trans-3-amino-4-oxo-2-phenyl-2,3,4,5-tetrahydro-1,5-benzothiazepine-5-acetamide which is produced in (v) of Example 1, 0.86 g of nicotinic acid and 1.44 g of dicyclohexylcarbodiimide. The mixture is stirred at room temperature for 22 hours. After the separated crystals are removed by filtration, the filtrate is concentrated under reduced pressure. The thus-obtained solid residue is washed with isopropyl ether, and recrystallized from ethanol to give 1.37 g of trans-3-nicotinamido-4-oxo-2-phenyl-2,3,4,5-tetrahydro-1,5-benzothiazepine-5-acetamide.

NMR spectrum (DMSO-$d_6$; ppm) $\delta = 4.12$ (d, 1H, J=16Hz), 4.66 (d, 1H, J=16Hz), 4.80 (d, 1H, J=12Hz), 5.05 (dd, 1H, J=8, 12Hz), 7.96 (m, 1H), 8.64 (m, 1H), 8.75 (m, 1H), 9.22 (d, 1H, 8Hz).

EXAMPLE 8

(i) A mixture of 17.7 g of N-trifluoroacetyl-α-dehydroleucine and 27 ml of acetic acid is heated to 155° C., and a mixture of 8.5 ml of o-aminobenzenethiol and 5 ml of acetic acid is added thereto dropwise slowly while stirring. The reaction mixture is stirred under heating for 2 hours, followed by concentration under reduced pressure. Isopropyl ether is added to the residue, and the resulting crystals are collected by filtration to give 10.5 g of 2-isopropyl-3-trifluoroacetamido-2,3-dihydro-1,5-benzothiazepin-4(5H)-one, m.p. 212°–215° C.

NMR spectrum (DMSO-$d_6$; ppm) $\delta = 0.72$ (d, 3H), 1.0 (d, 3H), 1.72–2.2 (m, 1H), 3.64 (dd, 1H), 4.39 (dd, 1H), 7.0–7.8 (4H).

(ii) In 200 ml of methanol is dissolved 10 g of 2-isopropyl 3-trifluoroacetamido-2,3-dihydro-1,5-benzothiazepin-4(5H)-one, whereto 75 ml of a 4 N aqueous solution of sodium hydroxide is added at room temperature. The reaction mixture is poured into ice water 2.5 hours later, and the precipitated organic substance is extracted with chloroform. The chloroform layer is washed with water and dried over magnesium sulfate. Thereafter, the solvent is distilled off under reduced pressure. Isopropyl ether is added to the residue, and the resulting crystals are collected by filtration to give 5.7 g of 3-amino-2-isopropyl-2,3-dihydro-1,5-benzothiazepin-4(5H)-one, m.p. 180°–183° C.

NMR spectrum (DMSO-$d_6$; ppm): $\delta = 0.74$ (d, 3H), 1.0 (d, 3H), 6.9–7.7 (4H).

(iii) By conducting the reaction in the same manner as in (iv) of Example 1 using 4 g of 3-amino-2-isopropyl-2,3-dihydro-1,5-benzothiazepin-4(5H)-one instead of trans-3-amino-2-phenyl-2,3-dihydro-1,5-benzothiazepin-4(5H)-one, crude oily substance is obtained. This oily substance is purified by silica gel column chromatography (elute; chloroform:methanol=100:1) to give 5.7 g of ethyl 3-amino-2-isopropyl-4-oxo-2,3,4,5-tetrahydro-1,5-benzothiazepine-5-acetate.

NMR spectrum (CDCl$_3$; ppm): δ=0.76 (d, 3H), 1.05 (d, 3H)., 1.3 (t, 3H), 1.7 (brs, 2H), 2.36-2.68 (m, 1H), 3.08 (dd, 1H), 3.45 (d, 1H, J=11Hz), 4.0 (d, 1H), 4.24 (q, 2H), 4.9 (d, 1H, J=17Hz), 7.0-8.0 (4H).

(iv) By conducting the reaction in the same manner as in (v) of Example 1 using 5.7 g of ethyl 3-amino-2-isopropyl-4-oxo-2,3,4,5-tetrahydro-1,5-benzothiazepine-5-acetate instead of ethyl trans-3-amino-4-oxo-2-phenyl-2,3,4,5 tetrahydro-1,5-benzothiazepine-5 acetate, crude oily substance is obtained as the residue of concentration. This oily substance is purified by silica gel column chromatography, and the elute is concentrated to give the solid residue, which is washed with isopropyl ether to give 2.9 g of 3-amino-2-isopropyl-4-oxo-2,3,4,5-tetrahydro-1,5-benzothiazepine-5-acetamide, m.p. 227°-229° C.

NMR spectrum (DMSO-d$_6$; ppm): δ=0.68 (d, 3H), 0.98 (d, 3H), 1.85 (brs, 2H), 3.88 (d, 1H, J=17Hz), 4.63 (d, 1H, J=17Hz), 7.0-7.7 (6H).

(v) A solution of 1 g of 3-amino-2-isopropyl-4-oxo-2,3,4,5-tetrahydro-1,5-benzothiazepine-5-acetamide and 1 g of succinimido 2-indolecarboxylate in 35 ml of dimethylformamide is stirred with heating at 70° C. Twenty-four hours later, the reaction mixture is concentrated under reduced pressure, whereto 50 ml of saturated sodium hydrogencarbonate and 50 ml of ethyl acetate are added. The mixture is stirred for a while. The resulting crystals are collected by filtration and recrystallized from a mixed solvent of dimethylformamidemethanol to give 0.92 g of 2-isopropyl 3-(2-indolecarboxamido)-4-oxo-2,3,4,5-tetrahydro-1,5-benzothiazepine-5 acetamide, the decomposition temperature being not less than 300° C.

NMR spectrum (DMSO-d$_6$; ppm): δ=0.73 (d, 3H), 1.02 (d, 3H), 1.9-2.3 (m, 1H), 3.48-3.76 (1H), 4.01 (d, 1H, J=17Hz), 4.4-4.9 (2H), 6.9-8.0 (11H), 8.87 (d, 1H), 11.5 (1H).

EXAMPLE 9

(i) A mixture of 3.4 g of O-methyl-N-2-naphthoyl-α-dehydrotyrosine methyl ester and 7 ml of acetic acid is heated to 155° C., whereto 4 ml of o-aminobenzenethiol is added dropwise slowly. After stirring under heating for 5 hours, the reaction mixture is concentrated under reduced pressure. A mixed solvent of isopropyl ether and ethyl acetate is added to the residue. The resulting crystals are collected by filtration to give 1.5 g of 2-p-methoxyphenyl-3-(2-naphthalenecarboxamido)-2,3-dihydro-1,5-benzothiazepin-4(5H)-one, m.p. 277°-280° C. (decomposition).

NMR spectrum (DMSO-d$_6$; ppm) δ=3.65 (s, 3H), 4.7-5.1 (2H), 6.7-8.3 (15H), 9.03 (d, 1H), 10.28 (s, 1H).

(ii) In the same manner as in (iv) of Example 1, 1.5 g of 2-p-methoxyphenyl-3-(2-naphthalenecarboxamido)-2,3-dihydro-1,5-benzothiazepin-4(5H)-one is dissolved in 30 ml of dimethylformamide, whereto 0.145 g of 60% sodium hydride is added under ice-cooling. After the mixture is stirred at room temperature for 30 minutes, 5 ml of dimethylformamide containing 0.45 ml of ethyl bromoacetate is added dropwise. The mixture is stirred at room temperature for 3 hours, and then the reaction mixture is concentrated under reduced pressure. Chloroform and water are added to the residue to separate the organic layer. The chloroform layer is washed with water and dried. The solvent is distilled off under reduced pressure. A mixed solvent of isopropyl alcohol-isopropyl ether is added thereto. The resulting crystals are collected by filtration to give 1.8 g of ethyl 2-p-methoxyphenyl-3-(2-naphthalenecarboxamido)-4-oxo-2,3,4,5-tetrahydro-1,5-benzothiazepine-5acetate, m.p. 183°-186° C.

NMR spectrum (DMSO-d$_6$; ppm): δ=1.16 (t, 3H), 3.64 (s, 3H), 4.08 (q, 2H), 4.3-5.2 (4H), 6.77 (d, 2H), 7.09 (d, 2H), 7.2-8.0 (10H), 8.24 (1H), 9.02 (d, 1H).

(iii) In 500 ml of methanol is dissolved 1.8 g of ethyl 2-p-methoxyphenyl- 3-(2-naphthalenecarboxamido)-4-oxo-2,3,4,5-tetrahydro-1,5-benzothiazepine-5-acetate, into which ammonia gas is blown under ice-cooling for about 1 hour. After the mixture is allowed to stand still at room temperature for 3 days, the reaction mixture is concentrated under reduced pressure to the volume of about 50 ml to give crystals. The crystals are collected by filtration to give 1.2 g of 2-p-methoxyphenyl-3-(2-naphthalenecarboxamido)-4-oxo-2,3,4,5-tetrahydro-1,5-benzothiazepine-5-acetamide, m.p. 243°-245° C.

NMR spectrum (DMSO-d$_6$; ppm): δ=3.64 (s., 3H), 4.08 (d, 1H, J=17Hz), 4.5-5.2 (3H), 6.76 (d, 2H), 7.09 (d, 2H), 7.2-8.0 (12H), 8.24 (1H), 9.06 (d, 1H).

EXAMPLE 10

(i) In 300 ml of methanol is dissolved 32 g of ethyl 3(R)-amino-4-oxo-2,3,4,5-tetrahydro-1,5-benzothiazepine-5-acetate ester which is produced in the method analogous to the known method, into which ammonia gas is blown under ice-cooling to the saturated state. The reaction temperature is allowed to elevate slowly to room temperature, and the reaction mixture is allowed to stand still for 24 hours. Thereafter, the resulting crystals are collected by filtration to give 28 g of 3(R)-amino-4-oxo-2,3,4,5-tetrahydro-1,5-benzothiazepine-5-acetamide, m.p. 223°-225° C. (decomposition).

NMR spectrum (DMSO-d$_6$; ppm): δ=1.86 (brs, 2H), 3.90 (d, 1H, J=18Hz), 4.62 (d, 1H, J=18Hz), 7.1-7.7 (6H).

(ii) With 50 ml of dichloromethane are mixed 2.6 g of succinimido γ-butyrolactone-γ(S)-carboxylate and 2.3 g of 3(R)-amino-4-oxo-2,3,4,5-tetrahydro-1,5-benzothiazepine-5-acetamide, and the mixture is stirred at room temperature for 4 hours. After the reaction mixture is allowed to stand overnight, a 5% aqueous solution of sodium hydrogencarbonate is added thereto. The mixture is stirred for a while, and then chloroform is added to separate the organic layer. The organic layer is washed with water, dried and concentrated under reduced pressure. The thus-obtained residue is purified by silica gel column chromatography to give 1.5 g of 3(R)-[γ-butyrolactone-γ(S)carboxamido]-4-oxo-2,3,4,5-tetrahydro-1,5-benzothiazepine-5-acetamide in the form of amorphous powders.

[α]$_D$= -214.3° (c=1.0%, chloroform).

NMR spectrum (CDCl$_3$; ppm): δ=3.0 (t, 1H), 7.1-7.8 (4H).

EXAMPLE 11

(i) A mixture of 19 g of N-benzyloxycarbonyl-β-(2-thienyl)-α-dihydroalanine and 30 ml of acetic acid is heated to 150° C., and then 20 ml of o-aminobenzenethiol is added to the mixture dropwise slowly. After the reaction mixture is stirred at the same temperature for 5 hours, it is concentrated under reduced pressure. A mixed solvent of isopropyl ether and ethyl acetate is added to the residue. The resulting crystals are collected by filtration to give 8.5 g of trans-3-benzyloxycarboxamido-2-(2 thienyl)-2,3-dihydro-1,5-benzothiazepin-4(5H)-one, m.p. 230°–231° C.

NMR spectrum (DMSO d6; ppm): δ=4.20 (dd, 1H, J=12Hz, 9Hz), 4.88 (s, 2H), 4.90 (d, 1H, J=12Hz), 6.7–7.7 (12H), 7.92 (d, 1H, J=9Hz).

On the other hand, the filtrate is concentrated under reduced pressure, and the residue is separated and purified by silica gel column chromatography to give 1.2 g of cis-3-benzyloxycarboxamido-2-(2-thienyl)-2,3-dihydro-1,5-benzothiazepin-4(5H)-one, m.p. 201°–202° C.

NMR spectrum (DMSO-d6;ppm): δ=4.50 (dd, 1H, J=8Hz, 7Hz), 4.97 (s, 2H), 5.49 (d, 1H, J=7Hz), 6.8–7.8 (12H).

(ii) To a mixture of 14.2 g of trans-3-benzyloxycarboxamido-2-(2-thienyl)-2,3-dihydro-1,5-benzothiazepin-4(5H)-one, 3.7 g of anisole and 60 ml of acetic acid is added 100 ml of 30% hydrobromic acid-acetic acid, and the mixture is stirred at room temperature for 1.5 hours. A mixed solvent of 200 ml of ether and 600 ml of isopropyl ether is added thereto, and the resulting crystals are collected by filtration to give 12.2 g of trans-3-amino-2-(2-thienyl)-2,3-dihydro-1,5-benzothiazepin-4(5H)-one hydrobromide, m.p. of the free base 188°–189° C.

NMR spectrum of the free base (DMSO-d6; ppm): δ=1.80 (s, 2H), 4.57 (d, 1H, J=10Hz), 6.7–7.6 (7H).

(iii) With 100 ml of dimethylformamide is mixed 12.2 g of trans-3-amino-2-(2-thienyl)-2,3-dihydro-1,5-benzothiazepin-4(5H)-one hydrobromide, and 2.7 g of 60% sodium hydride is added to the mixture under ice-cooling. The reaction temperature is gradually elevated to room temperature. The mixture is stirred for 2 hours. After the reaction mixture is cooled again to about 10° C., 5.7 g of ethyl bromoacetate is added dropwise. The reaction temperature is elevated to room temperature, and thereafter the mixture is stirred for one night and concentrated under reduced pressure. Ice water and ethyl acetate are poured to the residue to extract the organic substance. The ethyl acetate layer is washed with water, and dried. After the solvent is distilled off under reduced pressure, the obtained residue is purified by silica gel chromatography to give 8.0 g of ethyl trans-3-amino-4-oxo-2-(2-thienyl)-2,3,4,5-tetrahydro-1,5-benzothiazepine-5-acetate as oily substance.

NMR spectrum (CDCl3;ppm): δ=1.30 (t, 3H), 1.72 (s, 2H), 3.68 (d, 1H, J=10Hz), 3.9–4.5 (4H), 4.88 (d, 1H, J=18Hz), 6.7–7.8 (7H).

(iv) In 300 ml of methanol is dissolved 8 g of ethyl trans-3-amino-4-oxo-2-(2-thienyl)-2,3,4,5-tetrahydro-1,5-benzothiazepine-5-acetate, and ammonia gas is under ice-cooling blown into the solution until being saturated with ammonia gas. The reaction temperature is slowly elevated to room temperature, and the mixture is left standing for one day. Thereafter, the reaction mixture is concentrated under reduced pressure. Isopropyl alcohol is added to the obtained residue to crystallize. The crystals are collected by filtration to give 7 g of trans-3-amino-4-oxo-2-(2-thienyl)-2,3,4,5-tetrahydro-1,5-benzothiazepine-5-acetamide, m.p. 207°–210° C. (decomposition).

NMR spectrum (DMSO d6; ppm): δ=1.82 (brs, 2H), 3.91 (d, 1H, J=18Hz), 4.58 (d, 1H, J=1z), 4.67 (d, 1H, J=18Hz), 6.7–7.7 (7H).

(v) In 50 ml of dimethylformamide are dissolved 4 g of trans-3-amino-4-oxo-2-(2-thienyl)-2,3,4,5-tetrahydro-1,5-benzothiazepine-5-acetamide and. 3.3 g of succinimido γ-butyrolactone-γ(S)-carboxylate, and the solution is left standing still at room temperature for 2 days. The reaction mixture is concentrated under reduced pressure. To the residue are added 50 ml of a saturated solution of sodium hydrogencarbonate and 50 ml of ethyl acetate, and the mixture is stirred for a while. The resultant crystals are collected by filtration and the crystals are recrystallized from a mixed solvent of chloroform and methanol to give 2.1 g of A isomer of trans-3-[γ-butyrolactone-γ(S)-carboxamido]-4-oxo-2-(2-thienyl)-2,3,4,5-tetrahydro-1,5-benzothiazepine-5-acetamide. On the other hand, the ethyl acetate layer of the filtrate is washed with water and dried. After the solvent is distilled off under reduced pressure, isopropyl alcohol is added to the residue to crystallize. The resultant crystals are collected by filtration and the collected crystals are recrystallized from ethanol to give 1.5 g of B isomer of trans-3-[γ-butyrolactone γ(S)-carboxamido]-4-oxo-2-(2-thienyl)-2,3,4,5-tetrahydro-1,5-benzothiazepine-5-acetamide.

A isomer: m.p. 258°–263° C. (decomposition).

$[\alpha]_D = +573.7°$ (c=0.2%, DMSO).

NMR spectrum (DMSO-d6; ppm): δ=4.07 (d, 1H, J=17Hz), 4.4–5.1 (4H), 6.7–7.8 (9H), 8.93 (d, 1H).

B isomer: $[\alpha]_D = -497.4°$ (c=0.2%, DMSO).

NMR spectrum (DMSO-d6; ppm): δ=4.05 (d, 1H, J=17Hz), 4.3–4.9 (3H), 5.08 (d, 1H, J=11Hz), 6.7–7.8 (9H), 8.81 (d, 1H).

EXAMPLE 12

In 50 ml of dimethylformamide are dissolved 1.6 g of trans-3-amino-4-oxo-2-(2-thienyl)-2,3,4,5-tetrahydro-1,5-benzothiazepine-5-acetamide as obtained in (iv) of Example 11 and 1.3 g of succinimido 2-indolecarboxylate. The solution is stirred at 70° C. for 8 hours. The reaction mixture is concentrated under reduced pressure, and 50 ml of a saturated aqueous solution of sodium hydrogencarbonate and 50 ml of ethyl acetate are added to the residue. The mixture is stirred for a while. The resulting crystals are collected by filtration, followed by recrystallization from a mixed solvent of dimethylformamide and methanol to give 1.9 g of trans-3-(2-indolecarboxamido)-4-oxo-2-(2-thienyl)-2,3,4,5-tetrahydro-1,5-benzothiazepine-5-acetamide.

Decomposition temperature: not less than 270° C.

NMR spectrum (DMSO-d6; ppm): δ=4.08 (d, 1H, J=17Hz), 4.4–5.3 (3H), 6.6–7.7 (14H), 9.0 (d, 1H).

EXAMPLE 13

(i) To a mixture of 10 g of N-benzyloxycarbonyl-β-(p-chlorophenyl)-α-dehydroalanine ethyl ester and 20 ml of acetic acid is added 15 ml of o-aminobenzenethiol, and the mixture is stirred at 150° C. for 24 hours. The reaction mixture is concentrated under reduced pressure, and a mixed solvent of isopropyl ether and ethyl acetate is added to the residue. The resulting crystals are collected by filtration to give 3 g of 2-(p-chlorophenyl)-3-benzyloxycarboxamido-2,3-dihydro-1,5-benzothiazepin-4(5H)-one, m.p. 260°–263° C. (decomposition).

NMR spectrum (DMSO-d6; ppm): δ=4.1–4.7 (2H), 4.84 (s, 2H), 6.9–8.0 (14H).

(ii) To a mixture of 3.5 g of 2-(p-chlorophenyl)-3-benzyloxycarboxamido-2,3-dihydro-1,5-benzothiazepin-4(5H)-one, 860 mg of anisole and 50 ml of acetic acid is added 70 ml of 30% hydrobromic acid-acetic acid, and the mixture is stirred at room temperature for 3 hours. To the residue is added 300 ml of isopropyl ether. The resulting crystals are collected by filtration to give 3 g of 3-amino-2-(p-chlorophenyl)-2,3-dihydro-1,5-benzothiazepin-4(5H)-one hydrobromide, m.p. 201°–203° C. (decomposition).

NMR spectrum (DMSO-d6; ppm): δ=4.28 (d, 1H, J=11Hz), 4.78 (d, 1H, J=11Hz), 7.0–7.7 (8H).

(iii) With 50 ml of dimethylformamide is mixed 3 g of 3-amino-2-(p-chlorophenyl)-2,3-dihydro-1,5-benzothiazepin-4(5H) one hydrobromide, and 630 mg of 60% sodium hydride is added to the mixture under ice-cooling. After the reaction temperature is elevated to room temperature, the mixture is stirred for 3 hours. The reaction mixture is cooled to about 10° C. again, and 1.3 g of ethyl bromoacetate is added dropwise thereto. After the reaction temperature is elevated to room temperature, the mixture is stirred overnight, and then concentrated under reduced pressure. Ice-water and chloroform are added to the residue to extract the organic layer. The chloroform layer is washed with water, and dried, and then the solvent is distilled off under reduced pressure. The obtained residue is purified by silica gel column chromatography to give 1.5 g of ethyl 3-amino-2-(p-chlorophenyl)-4-oxo-2,3,4,5-tetrahydro-1,5-benzothiazepine-5-acetate.

NMR spectrum (DMSO-d6; ppm): δ=1.20 (t, 3H), 1.80 (brs, 2H), 3.4–4.9 (6H), 6.9–7.7 (8H).

(iv) In 200 ml of methanol is dissolved 1.5 g of ethyl 3-amino-2-(p-chlorophenyl)-4-oxo-2,3,4,5-tetrahydro-1,5-benzothiazepine-5-acetate, and ammonia gas is blown into the solution under ice-cooling up to the saturated state. The reaction temperature is slowly elevated to room temperature, and the reaction mixture is left standing overnight. Then, the reaction mixture is concentrated under reduced pressure. Ethyl acetate is added to the obtained residue, and the resulting crystals are collected by filtration to give 0.9 g of 3-amino-2-(p-chlorophenyl)-4-oxo-2,3,4,5-tetrahydro-1,5-benzothiazepine-5-acetamide, m.p. 217–220° C. (decomposition).

NMR spectrum (DMSO-d6; ppm): δ=1.72 (brs, 2H), 3.60 (d, 1H, J=11Hz), 3.94 (d, 1H, J=16Hz), 4.30 (d, 1H, J=11Hz), 4.70 (d, 1H, J=16Hz), 6.9–7.7 (10H).

(v) In 30 ml of dimethylformamide are dissolved 0.9 g of 3-amino-2-(p-chlorophenyl)-4-oxo-2,3,4,5-tetrahydro-1,5-benzothiazepine- 5-acetamide and 1.2 g of succinimido 2-indolecarboxylate, and the solution is stirred at 65° C. for 13 hours. The reaction mixture is concentrated under reduced pressure and a saturated aqueous solution of sodium hydrogencarbonate and ethyl acetate are added to the residue. The mixture is stirred for a while. The resulting crystals are collected by filtration, and the crystals are recrystallized from a mixed solvent of chloroform and methanol to give 0.8 g of 2-(p-chlorophenyl)-3-(2-indolecarboxamido)-4-oxo-2,3,4,5-tetrahydro-1,5-benzothiazepine-5-acetamide, m.p. 275°–290° C. (decomposition).

NMR spectrum (DMSO-d6; ppm): δ=4.11 (d, 1H, J=17Hz), 4.4–5.2 (3H), 6.8–7.8 (15H), 8.95 (d, 1H).

EXAMPLE 14

(i) In 250 ml of dimethylformamide is dissolved 13.9 g of trans-3-amino-2-phenyl-2,3-dihydro-1,5-benzothiazepin-4(5H)-one, and 2.3 g of 60% sodium hydride is added to the solution. After the mixture is stirred at room temperature for 20 minutes, 80 ml of a solution containing 10 g of tert-butyl bromoacetate in dimethylformamide is added thereto dropwise. The mixture is stirred at room temperature for 3 hours and then concentrated under reduced pressure. Water is added to the residue, and the organic substance is extracted with ethyl acetate. The ethyl acetate layer is washed with water and dried. Thereafter the solvent is distilled off under reduced pressure to give 18.6 g of tert-butyl trans-3-amino- 4-oxo-2-phenyl-2,3,4,5-tetrahydro-1,5-benzothiazepine-5-acetate in the form of white crystals, m.p. 172°–174° C.

NMR spectrum (CDCl3;ppm): δ=1.50 (s, 9H), 1.60 (brs, 2H), 3.83 (d, 1H, J=11Hz), 4.10 (d, 1H, J=17Hz), 4.15 (d, 1H, J=11Hz), 4.85 (d, 1H, J=17Hz), 7.0–7.8 (m, 9H).

(ii) In 300 ml of dimethylformamide are dissolved 18 g of tert-butyl trans-3-amino-4-oxo-2-phenyl-2,3,4,5-tetrahydro-1,5-benzothiazepine-5-acetate and 12 g of succinimido indolecarboxylate as synthesized by a known method, and the solution is stirred at 60° C. for 33.5 hours. The reaction mixture is poured to ice-water, and the mixture is stirred to separate crystals, which are collected by filtration and washed with water and dried to give 22 g of tert-butyl trans-3-(2-indolecarboxamido)-4-oxo-2-phenyl-2,3,4,5-tetrahydro-1,5-benzothiazepine-5-acetate, m.p. 196°–200° C. (decomposition).

NMR spectrum (DMSO-d6; ppm) δ=1.34 (s, 9H), 4.50 (d, 2H), 4.76 (d, 1H, J=12Hz), 5.06 (dd, 1H, J=8Hz, 12Hz), 6.78–7.78 (14H), 8.86 (d, 1H, J=8Hz), 11.24 (brs, 1H).

(iii) While a mixture of 5 g of tert-butyl trans-3-(2-indolecarboxamido)-4-oxo-2-phenyl-2,3,4,5-tetrahydro-1,5-benzothiazepine-5-acetate, 15 ml of acetic acid and 2 ml of anisole is stirred at room temperature, 21 ml of a 30% solution of hydrobromic acid-acetic acid is added to the mixture dropwise. After the mixture is stirred at room temperature for 9 hours, the resulting crystals are collected by filtration and washed with ethyl acetate to give 3.5 g of trans-3-(2-indolecarboxamido)- 4-oxo-2-phenyl-2,3,4,5-tetrahydro-1,5-benzothiazepine-5-acetic acid, m.p. 260°–270° C. (decomposition).

NMR spectrum (DMSO-d6; ppm): δ=4.30 (d, 1H, J=17Hz), 4.71 (d, 1H, J=17Hz), 4.76 (d, 1H, J=12Hz), 5.10 (dd, 1H, J=10Hz, 12Hz), 6.7–7.8 (14H), 8.86 (d, 1H, J=10Hz), 11.24 (brs, 1H), 12.18 (brs, 1H).

(iv) While a mixture of 2 g of trans-3-(2-indolecarboxamido)-4-oxo-2-phenyl-2,3,4,5-tetrahydro-1,5-benzothiazepine-5-acetic acid, 20 ml of dichloromethane and 0.2 g of 2-phenylethylamine and tri-n-butylamine is stirred at room temperature, 1.2 g of 2-chloro-N-methylpyridinium iodide is added to the mixture. The mixture is stirred at room temperature for 18 hours. After chloroform is added to the reaction mixture, the mixture is washed with a 5% aqueous solution of hydrochloric acid, a saturated aqueous solution of sodium hydrogencarbonate and a saturated solution of sodium chloride. Thereafter, the mixture is dried, and the solvent is distilled off under reduced pressure. The obtained residue is separated and purified by silica gel column chromatography (eluent: chloroform), and recrystallized from ethanol to give 0.7 g of trans-3-(2-indolecarboxamido)-4-oxo-2-phenyl-N-(2-phenylethyl)-2,3,4,5-tetrahydro 1,5-benzothiazepine-5-acetamide ½hydrate, m.p. 157°–163° C.

NMR spectrum (CDCl3;ppm): δ=2.82 (t, 2H, J=6Hz), 3.59 (m, 2H), 4.41 (d, 1H, J=12Hz), 4.59 (2H), 5.11 (dd, 1H, J=8Hz, 12Hz), 6.55 (d, 1H, J=2Hz), 6.8–7.9 (20H), 8.75 (brs, 1H).

EXAMPLE 15

While a mixture of 0.2 g of trans-3-(2-indolecarboxamido)-4-oxo-2-phenyl-2,3,4,5-tetrahydro-1,5-benzothiazepine-5-acetic acid as obtained in (iii) of Example 14, 2 ml of dichloromethane, 45 mg of methylamine hydrochloride and 0.32 g of tri-n-butylamine is stirred at room temperature, 0.13 g of 2-chloro-N-methyl-pyridinium iodide is added to the mixture. The mixture is stirred at room temperature for 23 hours. After the solvent is distilled off under reduced pressure, the residue is washed with isopropyl ether several times, and ethyl acetate is added thereto. The mixture is washed with a 5% aqueous solution of hydrochloric acid, a saturated aqueous solution of sodium hydrogencarbonate and a saturated aqueous solution of sodium chloride, and dried. After the solvent is distilled off, the obtained residue is recrystallized from ethyl acetate to give 60 mg of trans-3-(2-indolecarboxamido)-N-methyl-4-oxo-2-phenyl-2,3,4,5-tetrahydro-1,5-benzothiazepine-5-acetamide, m.p. 195° C. (decomposition).

NMR spectrum (CDCl$_3$;ppm): $\delta = 2.82$ (d, 3H, J=6Hz), 4.37 (d, 1H, J=16Hz), 4.59 (d, 1H, J=12Hz), 4.9 (d, 1H, J=16Hz), 5.15 (dd, 1H, J=8Hz, 12Hz), 6.51 (d, 1H, J=3Hz), 6.8-7.8 (15H), 8.56 (brs, 1H).

EXAMPLE 16

While a mixture of 0.5 g of trans-3-(2-indolecarboxamido)-4-oxo-2-phenyl-2,3,4,5-tetrahydro 1,5-benzothiazepine-5 -acetic acid as obtained in (iii) of Example 14, 10 ml of dimethylformamide, 0.11 g of pyrrolidine and 0.5 g of tri-n-butylamine is stirred at room temperature, 0.5 g of 2-chloro-N-methylpyridinium iodide to the mixture. The mixture is stirred at room temperature for 2.5 hours. After the solvent is distilled off, chloroform is added to the residue. The mixture is washed with a 5% aqueous solution of hydrochloric acid, a saturated solution of sodium hydrogencarbonate and a saturated aqueous solution of sodium chloride, and dried. After the solvent is distilled off under reduced pressure, the residue is recrystallized from a mixed solvent of chloroform and methanol to give 0.15 g of trans-3-(2-indolecarboxamido)-2-phenyl-5-(1-pyrrolidinylcarbonylmethyl)-2,3-dihydro-1,5-benzothiazepin-4(5H)-one, m.p. 282°-284° C. (decomposition).

NMR spectrum (CDC$_3$; ppm): $\delta = 1.5-2.1$ (4H), 3.2-3.7 (4H), 4.10 (d, 1H, J=16Hz), 4.50 (d, 1H, J=10Hz), 5.00 (d, 1H, J=16Hz), 5.38 (dd, 1H, J=8Hz, 10Hz), 6.62 (d, 1H, J=2Hz), 6.8-7.8 (14H), 8.80 (brs, 1H).

EXAMPLE 17

While a mixture of 0.5 g of trans-3-(2-indolecarboxamido)-4-oxo-2 phenyl-2,3,4,5-tetrahydro-1,5 benzothiazepine-5-acetic acid as obtained in (iii) of Example 14, 20 ml of dimethylformamide, 0.14 g of morpholine and 0.5 g of tri-n-butylamine is stirred at room temperature, 0.45 g of 2-chloro-N methylpyridinium iodide is added to the mixture, and the mixture is stirred at 45° C. for 6 hours. After the solvent is distilled off under reduced pressure, chloroform is added to the residue. The mixture is washed with a 5% aqueous solution of hydrochloric acid, a saturated aqueous solution of sodium hydrogencarbonate and a saturated aqueous solution of sodium chloride, and dried. After the solvent is distilled off under reduced pressure, the residue is recrystallized from a mixed solvent of chloroform and methanol to give 0.26 g of trans-3-(2-indolecarboxamido)-2-phenyl-5-(morpholinocarbonylmethyl)-2,3-dihydro-1,5-benzothiazepin-4(5H)-one monohydrate, m.p. 274°-277° C. (decomposition).

NMR spectrum (CDCl$_3$-CD$_3$OD;ppm) $\delta = 4.37$ (d, 1H, J=16Hz), 4.51 (d, 1H, 12Hz), 4.97 (d, 1H, J=16Hz), 5.29 (dd, 1H, J=9Hz, 12Hz), 6.8-7.9 (15H), 8.94 (brs, 1H).

EXAMPLE 18

(i) In 300 ml of methanol is dissolved 11 g of ethyl 3-amino-2-oxo-2,3,4,5-tetrahydro-1H-1-benzazepine-1-acetate which can be produced in accordance with the known method, and ammonia gas is blown into the solution under ice-cooling. The reaction mixture is left standing in the refrigerator for 3 days, and thereafter concentrated under reduced pressure. Isopropyl ether is added to the residue. The resulting crystals are collected by filtration to give 4.2 g of 3-amino-2-oxo-2,3,4,5-tetrahydro-1H-1-benzazepine-1-acetamide, m.p. 198°-200° C. (decomposition).

IR$_{max}$ (KBr, cm$^{-1}$): 3370, 3310, 3175, 1705, 1665.

(ii) In 70 ml of dichloromethane, 2.0 g of 3 amino 2-oxo- 2,3,4,5-tetrahydro-1H-1-benzazepine-1-acetamide and 2.5 g of succinimido $\gamma$-butyrolactone-$\gamma$(S)-carboxylate are mixed, and the mixture is stirred at room temperature for 6 hours. The reaction mixture comes to dissolve gradually. After the completion of the reaction, 100 ml of a saturated aqueous solution of sodium hydrogencarbonate is added. The mixture is stirred for a while. The resulting crystals are collected by filtration. The organic layer of the filtrate is separated from the water layer. After the organic layer is washed with water and dried, the solvent is distilled off under reduced pressure. The residue is purified by silica gel column chromatography. The eluent is concentrated under reduced pressure. Isopropyl ether is added to the obtained residue, and the resulting crystals are collected by filtration and combined with the crystals as obtained above. The combined crystals are recrystallized from a mixed solvent of chloroform and isopropyl ether to give 0.25 g of 3-[$\gamma$-butyrolactone-$\gamma$(S)-carboxamido]-2-oxo-2,3,4,5-tetrahydro-1H-1-benzazepine-1-acetamide hemihydrate, m.p. 165°-182° C.

IR$_{max}$ (KBr, cm$^{-1}$): 3400, 3330, 1790, 1660.

$[\alpha]_D = +32°$ (c=0.5%, DMSO).

EXAMPLE 19

By following the same reaction procedure and treatment procedure as in Example 3 using 3.27 g of cis-3-amino-4 oxo-2-phenyl-2,3,4,5-tetrahydro-1,5-benzothiazepine-5-acetamide as obtained in (iii) of Example 2 and 1.29 g of L-pyroglutamic acid, reaction product of mixed diastereomer is obtained. This mixture is separated and purified by silica gel column chromatography (elute:chloroform/methanol=30:1) to give 400 mg of B isomer of cis-4-oxo-3(R)-[5-oxo-2(S)-pyrrolidinecarboxamido]-2(R)-phenyl-2,3,4,5-tetrahydro-1,5-benzothiazepine-5-acetamide in white crystalline powder and 190 mg of A isomer of cis-4-oxo 3(S)-[5 oxo-2(S)-pyrrolidinecarboxamido]-2(S)-phenyl-2,3,4,5-tetrahydro-1,5-benzothiazepine-5-acetamide in white non-crystalline powder.

A isomer:

NMR spectrum (DMSO-d$_6$; ppm) $\delta = 1.43$ (m, 1H), 1.85-2.1 (m, 3H), 4.05-4.10 (2H), 4.73-4.78 (2H), 5.09 (m, 1H, J=7.3Hz), 7.27 (1H), 7.36-7.42 (6H), 7.56-7.63 (4H), 7.68 (d, 1H], 7.75 (d, 1H).

$[\alpha]_D = +140°$ (c=0.1%, DMSO)

B isomer (recrystallized from ethanol): m.p. 250°-253° C. (decomposition).

NMR spectrum (DMSO-d$_6$; ppm): $\delta = 1.62-1.76$ (m, 2H), 1.86-1.94 (m, 1H), 2.90-2.2 (m, 1H), 3.93 (1H), 4.11 (d, 1H, J=16.6Hz), 4.72-4.79 (2H), 5.11 (d, 1H, J=7.3Hz), 7.19 (d, 1H, J=7.3Hz), 7.29 (1H), 7.37 (6H), 7.61 (2H), 7.65 (1H), 7.76 (d, 1H, J=7.3Hz), 7.94 (s, 1H).

$[\alpha]_D = -157°$ (c=0.1%, DMSO).

EXAMPLE 20

In 30 ml of chloroform are dissolved 1.64 g of trans-3-amino-4-oxo-2-phenyl-2,3,4,5-tetrahydro-1,5-benzothiazepine-5-acetamide as obtained in (v) of Example 1 and 1.4 ml of triethylamine, whereto 0.6 ml of benzoyl chloride is added under stirring at room temperature, and the mixture is stirred for 6 hours. After a solution of sodium hydrogencarbonate is added to the reaction mixture, the separated crystals are removed by filtration. The obtained crystals are recrystallized from methanol to give 1.25 g of trans-3-benzamido-4-oxo-2-phenyl-2,3,4,5-tetrahydro-1,5-benzothiazepine-5-acetamide as white crystalline powder, m.p. 246°–248° C.

NMR spectrum (DMSO-d₆; ppm): δ=4.09 (d, 1H, J=17Hz), 4.66 (d, 1H, J=17Hz), 4.7–5.2 (2H), 7.0–7.8 (16H), 8.92 (d, 1H, J=8Hz).

EXAMPLE 21

The same reaction procedure and treatment procedure as in Example 20 using 1.64 g of trans-3-amino-4-oxo-2-phenyl-2,3,4,5-tetrahydro-1,5-benzothiazepine-5-acetamide as obtained in (v) of Example 1 and 0.67 ml of p-chlorobenzoyl chloride is carried out to give 1.6 g of trans-3-p-chlorobenzamido-4-oxo-2-phenyl-2,3,4,5-tetrahydro-1,5-benzothiazepine-5-acetamide as white crystal powder, m.p. 272°–275° C.

NMR spectrum (DMSO-d₆; ppm): δ=4.08 (d, 1H, J=17Hz), 4.65 (d, 1H, J=17Hz), 4.7–5.2 (2H), 7.0–7.7 (16H), 9.03 (d, 1H, J=8Hz).

EXAMPLE 22

(i) A mixture of 35 g of ethyl 2-benzyloxycarboxamido-4-phenyl-2-butenate and 50 ml of acetic acid is heated to 150° C., and 17 ml of o-aminobenzenethiol is added to the mixture. After stirring the mixture for 6 hours, the reaction mixture is distilled off under reduced pressure, and isopropyl ether is added to the residue. The resulting crystals are collected by filtration to give 10 g of 2-benzyl-3-benzyloxycarboxamido-2,3-dihydro-1,5-benzothiazepin-4(5H)-one, m.p. 215°–216° C.

NMR spectrum (DMSO-d₆; ppm) δ=5.00 (s, 2H), 6.9–7.6 (m, 14H), 8.02 (d, 1H, J=6Hz).

(ii) To a mixture of 10.9 g of 2-benzyl-3-benzyloxycarboxamido-2,3-dihydro-1,5-benzothiazepin-4(5H)-one, 2.8 ml of anisole and 14 ml of acetic acid is added 47 ml of 30% hydrogen bromideacetic acid under water cooling, and the mixture is stirred for 6 hours as in (iii) of Example 1. After the completion of the reaction, 150 ml of isopropyl ether is added thereto, and the resulting crystals are collected by filtration. After the thus-obtained crystals are washed with isopropyl ether, they are added to a mixed solution of 100 ml of a 15% aqueous solution of sodium hydrogencarbonate and 1000 ml of chloroform. The solid substance is extracted, and the chloroform layer is washed with water and dried over magnesium sulfate. The solvent is distilled off under reduced pressure to give 7.1 g of 3-amino-2-benzyl-2,3-dihydro-1,5-benzothiazepin-4(5H)-one, m.p. 223°–224° C.

NMR spectrum (CDC₃; ppm): δ=1.75 (brs, 1H), 2.5–2.9 (1H), 3.1–3.3 (2H), 3.45 (d, 1H, J=12Hz), 7.0–7.7 (9H), 7.85 (brs, 1H).

(iii) In 90 ml of dimethylformamide are suspended 7.1 g of 3-amino-2-benzyl-2,3-dihydro-1,5-benzothiazepin-4(5H)-one, and 1.1 g of 60% sodium hydride is added to the mixture. To the obtained solution is added a solution of 3.05 ml of ethyl bromoacetate and 10 ml of dimethylformamide dropwise for 30 minutes under ice-cooling. The reaction temperature is allowed to elevate slowly to room temperature, and the mixture is stirred for 7.5 hours, and then concentrated under reduced pressure. By adding water and chloroform to the residue, organic substance is extracted. After the chlorofrom layer is dried, the solvent is distilled off under reduced pressure. The obtained oily product is dissolved in 300 ml of methanol, into which ammonia gas is blown to the level of saturation under ice-cooling. The reaction temperature is again elevated to room temperature, and the mixture is allowed to stand still for two days. Then, the reaction mixture is concentrated under reduced pressure. The white crystals are collected by filtration to give 4.29 g of 3-amino-2-benzyl-4-oxo-2,3,4,5-tetrahydro-1,5-benzothiazepine-5-acetamide, m.p. 233° C.

NMR spectrum (CDC₃; ppm): δ=1.5–1.9 (2H), 2.65 (1H), 4.26 (d, 1H, J=17Hz), 4.80 (d, 1H, J=17Hz), 5.37 (brs, 1H), 7.05 (brs, 1H), 7.2–7.7 (9H).

(iv) In a mixture of 150 ml of dichloromethane and 30 ml of dimethylformamide are dissolved 1.77 g of succinimido 2 indolecarboxylate as obtained in accordance with a known method and 2.01 g of 3-amino-2-benzyl-4-oxo-2,3,4,5-tetrahydro-1,5-benzothiazepine-5-acetamide as obtained in (iii) described above, and the mixture is heated to 70° C. After the mixture is stirred for 8 hours, isopropyl ether is added to the reaction mixture to yield solid substance. The crude product obtained by filtration is recrystallized from a mixed solvent of dimethylformamide and isopropyl ether to give 1.94 g of 2-benzyl-3-(2-indolecarboxamido)-4-oxo-2,3,4,5-tetrahydro-1,5-benzothiazepine-5-acetamide ½ dimethylformamide adduct, m.p. 275° C.

NMR spectrum (CDC₃; ppm): δ=2.65 (dd, 1H, J=11Hz, 14Hz), 3.25 (dd, 1H, J=2.5Hz, 14Hz), 3.83 (ddd, 1H, J=2.5Hz, 11Hz, 11Hz), 4.12 (d, 1H, J=17Hz), 4.58 (dd, 1H, J=8Hz, 11Hz), 4.78 (d, 1H, J=17Hz), 6.59 (brs, 1H), 9.01 (d, 1H, J=8Hz), 10.77 (brs, 1H).

EXAMPLE 23

(i) In 100 ml of ethanol is dissolved 20.5 g of 2-amino-5chlorobenzenethiol and 28.2 g of N benzyloxycarbonyl-α-dehydro-β-phenylalanine, and the mixture is stirred under reflux for 48 hours. After the completion of the reaction, the reaction mixture is concentrated under reduced pressure. To the obtained residue is added 200 ml of xylene, and the mixture is stirred under reflux for 6 hours with water being removed. After the completion of the reaction, the mixture is cooled at room temperature. The separated crystals are collected by filtration and washed with isopropyl alcohol to give 20.0 g of 3-benzyloxycarboxamido-8-chloro-2-phenyl-2,3-dihydro-1,5-benzothiazepin-4(5H)-one, m.p. 179°–198° C.

(ii) In 200 ml of dimethylformamide is dissolved 20.0 g of 3-benzyloxycarboxamido-8-chloro-2-phenyl-2,3-dihyro-1,5-benzothiazepin-4(5H)-one, and 1.91 g of 60% sodium hydride is added. After the mixture is stirred at room temperature for 30 minutes, the reaction mixture is ice-cooled, and 50 ml of dimethylformamide containing 7.6 g of ethyl bromoacetate is added dropwise. The temperature of the mixture is elevated to room temperature, and the mixture is stirred for 5 hours, followed by concentration under reduced pressure. By adding ice-water and chloroform to the residue, the organic substance is extracted. The chloroform layer is washed with water and dried. Thereafter, the solvent is distilled off under reduced pressure, and separated and purified by silica gel chromatography (elute: chloroform) to give 11.0 g of ethyl cis-3-benzyloxycarboxamido-8-chloro-4-oxo-2-phenyl-2,3,4,5-tetrahydro-1,5-benzothiazepine-5-acetate and 3.3 g of ethyl trans-3-benzyloxycarboxamido-8 chloro-4-oxo-2-phenyl-2,3,4,5-tetrahydro-1,5-benzothiazepine-5-acetate.

Cis form:
NMR spectrum (CDC$_3$; ppm): $\delta$=1.29 (t, 3H), 4.25 (d, 1H), 4.26 (q, 2H), 4.73 (t, 1H), 4.79 (d, 1H), 4.94 (d, 1H), 5.03 (d, 1H), 5.12 (d, 1H), 5.22 (d, 1H), 7.2-7.5 (m, 12H), 7.72 (d, 1H).

Trans form:
NMR spectrum (CDC$_3$; ppm): $\delta$=1.27 (t, 3H), 4.1-4.3 (m, 4H), 4.7-4.9 (m, 4H), 5.57 (d, 1H), 7.1-7.5 (m, 12H), 7.67 (d, 1H).

(iii) To a mixture of 11.0 g of ethyl cis-3-benzyloxycarboxamido-8-chloro-4-oxo-2-phenyl-2,3,4,5-tetrahydro-1,5-benzothiazepine-5-acetate, 2.3 g of anisole and 11 ml of acetic acid is added 38 ml of 30%-hydrogen bromide-acetic acid, and the mixture is stirred at room temperature for 3.5 hours. After the completion of the reaction, hexane and isopropyl ether is added thereto, and the resulting crystals are collected by filtration. Ethyl acetate and a saturated sodium hydrogencarbonate solution are added to the obtained crystals. After the mixture is stirred under ice-cooling, the organic layer is separated, washed with water, dried, and concentrated under reduced pressure to give 6.9 g of ethyl cis-3-amino-8-chloro-4-oxo-2-phenyl-2,3,4,5-tetrahydro 1,5-benzothiazepine-5-acetate.

NMR spectrum (CDC$_3$; ppm): $\delta$=1.34 (t 3H), 1.58 (brs, 2H), 3.86 (d, 1H), 4.16 (d, 1H) 4.27 (q, 2H), 4.89 (d, 1H), 4.90 (d, 1H), 7.24 (m, 7H), 7.71 (d, 1H).

(iv) In 220 ml of methanol is dissolved 6.9 g of ethyl cis-3-amino-8-chloro-4-oxo-2-phenyl-2,3,4,5-tetrahydro-1,5-benzothiazepine-5-acetate, into which ammonia gas is blown to the level of saturation under ice-cooling. The reaction temperature is slowly elevated to room temperature, and the mixture is allowed to stand still overnight. Then, the reaction mixture is concentrated under reduced pressure. The separated crystals are collected by filtration to give 6.2 g of cis-3-amino-8-chloro-4-oxo-2-phenyl-2,3,4,5-tetrahydro-1,5-benzothiazepine-5-acetamide.

NMR spectrum (CDC$_3$; ppm): $\delta$=3.85 (d, 1H), 4.46 (d, 1H) 4.67 (d, 1H), 4.89 (d, 1H), 5.95 (brs, 1H), 6.98 (brs, 1H), 7.25-7.55 (m, 7H), 7.73 (d, 1H).

(v) With 114 ml of dichloromethane are mixed 5.7 g of cis-3-amino-8-chloro-4-oxo-2-phenyl-2,3,4,5-tetrahydro-1,5-benzothiazepine-5-acetamide and 4.1 g of succinimido $\gamma$-butyrolactone-$\gamma$(S)-carboxylate. While the mixture is stirred at room temperature for 6 hours, the reaction mixture gradually comes to dissolve. After the completion of the reaction, a 5% aqueous solution of sodium hydrogencarbonate is added thereto and the mixture is stirred for a while under ice-cooling to yield crystals The crude crystals obtained by filtration are recrystallized from a mixed solvent of isopropyl alcohol and chloroform to give 2.5 g of B isomer $\frac{1}{2}$ chloroform $\frac{1}{2}$ isopropyl alcohol solvate of cis-3-[$\gamma$-butyrolactone-$\gamma$(S)-carboxamido]-8-chloro-4-oxo-2-phenyl-2,3,4,5-tetrahydro-1,5-benzothiazepine-5-acetamide. Meanwhile, the organic layer separated from the filtrate by adding chloroform thereto is washed with water and dried over magnesium sulfate. After the solvent is distilled off under reduced pressure, isopropyl ether is added to the residue. The separated crystals are recrystallized from isopropyl alcohol to give 1.5 g of A isomer $\frac{1}{2}$ isopropyl alcohol solvate of cis-3-[$\gamma$-butyrolactone-$\gamma$(S)-carboxamido]-8-chloro-4-oxo-2-phenyl-2,3,4,5-tetrahydro-1,5-benzothiazepine-5-acetamide.

A isomer: m.p. 125°-127° C.
NMR spectrum (CDC$_3$; ppm): $\delta$=2.14 (m, 1H), 2.38-2.49 (m, 3H), 4.45 (d, 1H), 4.58 (t, 1H), 4.65 (d, 1H), 4.83, (t, 1H), 5.20 (d, 1H), 5.74 (brs, 1H), 6.69 (d, 1H), 6.88 (brs, 1H), 7.32-7.53 (m, 7H), 7.79 (d, 1H)
$[\alpha]_D$= +107.8° (c=0.1%, DMSO).

B isomer: m.p. 198°-200° C.
NMR spectrum (CDC$_3$; ppm): $\delta$=1.90-2.01 (m, 2H), 2.24-2.43 (m, 2H), 4.50 (d, 1H), 4.60-4.64 (m, 2H), 4.83, (t, 1H), 5.23 (d, 1H), 5.66 (brs, 1H), 6.81 (brs, 1H), 6.89 (d, 1H), 7.31-7.54 (m, 7H), 7.78 (d, 1H).
$[\alpha]_D$= -96.7° (c=0.1%, DMSO).

EXAMPLE 24

(i) To a mixture of 3.3 g of ethyl trans-3-bezyloxycarboxamido-8-chloro-4-oxo-2-phenyl-2,3,4,5-tetrahydro-1,5 benzothiazepine-5-acetate as obtained in (ii) of Example 23, 0.68 g of anisole and 3.3 ml of acetic acid is added 11.4 ml of 30% hydrogen bromide-acetic acid as in (iii) of Example 23, and the mixture is stirred at room temperature for 2.5 hours. After the completion of the reaction, hexane and isopropyl ether is added thereto and the resulting crystals are collected by filtration. Ethyl acetate and a saturated aqueous solution of sodium hydrogencarbonate are added to the obtained crystals. After the mixture is stirred under ice-cooling, the organic layer is separated, washed with water, dried, and concentrated under reduced pressure to give 1.7 g of ethyl trans-3-amino-8-chloro-4-oxo-2-phenyl-2,3,4,5-tetrahydro-1,5-benzothiazepine-5-acetate, m.p. 173°-175° C.

NMR spectrum (CDC$_3$; ppm): $\delta$=1.32 (t, 3H), 1.59 (brs, 2H), 3.85 (d, 1H), 4.06-4.37 (4H), 4.88 (d, 1H), 7.04-7.62 (8H).

(ii) In the same manner as in (iv) of Example 23, 1.7 g of ethyl trans-3-amino-8-chloro-4-oxo-2-phenyl-2,3,4,5-tetrahydro-1,5-benzothiazepine-5-acetate is dissolved in 50 ml of methanol, into which ammonia gas is blown to the level of saturation under ice-cooling. The reaction temperature is slowly elevated to room temperature, and the mixture is allowed to stand still overnight. Then, the reaction mixture is concentrated under reduced pressure. The separated crystals are collected by filtration to give 1.4 g of trans-3-amino-8-chloro-4-oxo-2-phenyl-2,3,4,5-tetrahydro-1,5-benzothiazepine-5-acetamide, m.p. 225°-228° C.

NMR spectrum (CDC$_3$; ppm): $\delta$=4.22 (d, 1H) 4.38 (d, 1H), 4.72 (d, 1H), 5.74 (brs, 1H), 6.95 (brs, 1H), 7.04-7.66 (m, 8H).

(iii) With 25 ml of dichloromethane are mixed 1.4 g of trans-3-amino-8-chloro-4-oxo-2-phenyl-2,3,4,5-tetrahydro-1,5 benzothiazepine-5-acetamide and 0.97 g of succinimido $\gamma$-butyrolactone-$\gamma$(S)-carboxylate as in (v) of Example 23. While the mixture is stirred at room temperature for 6 hours, the reaction mixture gradually comes to dissolve. After the completion of the reaction, a 5% aqueous solution of sodium hydrogencarbonate is added thereto and the mixture is stirred for a while under ice-cooling to yield crystals. The crude crystals obtained by filtration are recrystallized from a mixed solvent of isopropyl alcohol and chloroform to give 0.3 g of A isomer of trans-3-[γ-butyrolactone-γ(S)-carboxamido]-8-chloro-4-oxo-2-phenyl-2,3,4,5-tetrahydro-1,5-benzothiazepine-5-acetamide. Meanwhile, the organic layer separated from the filtrate by adding chloroform is washed with water and dried over magnesium sulfate. After the solvent is distilled off under reduced pressure, isopropyl ether is added to the residue. The separated crystals are recrystallized from isopropyl alcohol to give 0.3 g of B isomer of trans-3-[γ-butyrolactone-γ(S)-carboxamido]-8-chloro-4-oxo-2-phenyl-2,3,4,5-tetrahydro-1,5-benzothiazepine-5-acetamide.

A isomer: m.p. 270°–276° C.
NMR spectrum (CDCl$_3$+CD$_3$OD;ppm): δ=1.88 (m, 1H), 2.23–2.49 (m, 3H), 4.27 (d, 1H), 4.55–4.64 (2H), 4.68 (d, 1H), 5.01 (d, 1H), 7.07–7.58 (8H).
$[α]_D$= +370.1° (c=0.1%, DMSO).

B isomer: m.p. 190°–195° C.
NMR spectrum (CDC13+CD30D;ppm): δ=1.68–1.72 (m, 1H), 1.85–1.95 (m, 1H), 2.25–2.47 (2H), 4.34 (d, 1H), 4.58–4.62 (3H), 4.99–5.12 (1H), 7.10–8.00 (8H).
$[α]_D$= −119.0° (c=0.1%, DMSO).

EXAMPLE 25

By conducting the same reaction and treatment as in Example 3 using 2.1 g of cis-3-amino-8-chloro-4-oxo-2-phenyl-2,3,4,5-tetrahydro-1,5-benzothiazepine-5-acetamide as obtained in (iv) of Example 23, 0.75 g of L-pyroglutamic acid and 1.26 g of dicyclohexylcarbodiimide, 0.92 g of A isomer.½ hydrate and 0.43 g of B isomer.½ isopropyl alcohol solvate.½ hydrate of cis-8-chloro-4-oxo-3-[5-oxo-2(S)-pyrrolidinecarboxamide]-2-phenyl-2,3,4,5-tetrahydro-1,5-benzothiazepine-5-acetamide are obtained respectively.

A isomer: m.p. 165°–176° C.
NMR spectrum (CDC$_3$; ppm): δ=1.66 (m, 2H), 2.17 (m, 2H), 3.88 (m, 1H), 4.41 (d, 1H), 4.65 (d, 1H), 4.84 (t, 1H), 5.21 (d, 1H), 5.91 (brs, 1H), 5.97 (brs, 1H), 6.43 (brs, 1H), 6.91 (brs, 1H), 7.3–7.5 (m, 7H), 7.78 (d, 1H)
$[α]_D$= +116.4° (c=0.1%, DMSO).

B isomer: m.p. 160°–171° C.
NMR spectrum (CDC$_3$; ppm): δ=1.60 (m, 1H), 1.74 (m, 1H), 1.96 (m, 1H), 2.25 (m, 1H), 3.90, (dd, 1H), 4.48 (d, 1H), 4.71 (d, 1H), 4.86 (t, 1H), 5.28 (d, 1H), 6.91 (d, 1H), 6.95 (brs, 1H), 7.14 (brs, 1H), 7.3–7.5 (m, 7H), 7.78 (d, 1H).
$[α]_D$= −123.9° (c=0.1%, DMSO).

EXAMPLE 26

By conducting the same reaction and treatment as in Example 3 using 1.7 g of trans-3-amino-8-chloro-4-oxo-2-phenyl-2,3,4,5-tetrahydro-1,5-benzothiazepine-5-acetamide as obtained in (ii) of Example 24, 0.6 g of L-pyroglutamic acid and 1.0 g of dicyclohexylcarbodiimide, 0.29 g of A isomer.1/2 isopropyl alcohol solvate and 0.3 g of B isomer 1/2 hydrate of trans-8-chloro-4-oxo-3-[5-oxo-2(S)-pyrrolidinecarboxamide]-2-phenyl-2,3,4,5-tetrahydro-1,5-benzothiazepine-5-acetamide are obtained respectively.

A isomer: m.p. 176°–190° C.
NMR spectrum (CDC$_3$; ppm): δ=1.35 (m, 1H), 2.04 (m, 3H), 3.91 (m, 1H), 4.19 (d, 1H), 4.60 (d, 1H), 4.65 (d, 1H), 5.00 (dd, 1H), 6.70 (brs, 1H), 7.1–7.7 (m, 10H), 8.34 (brs, 1H)
$[α]_D$= +407.9° (c=0.1%, DMSO).

B isomer: m.p. 183°–205° C.
NMR spectrum (CDC$_3$; ppm): δ=1.08 (m, 1H), 2.06 (m, 2H), 2.37 (m, 1H), 3.82 (d, 1H), 3.95 (m, 1H), 4.70 (d, 1H), 4.72 (d, 1H), 5.28 (dd, 1H), 6.09 (brs, 1H), 6.85 (brs, 1H), 7.2–7.4 (m, 6H), 7.46 (d, 1H), 7.71 (d, 1H), 7.90 (d, 1H), 8.47 (d, 1H).
$[α]_D$= −413.6° (c=0.1%, DMSO).

EXAMPLE 27

By conducting the same reaction and treatment as in (v) of Example 13 using 0.3 g of cis-3 amino-8-chloro-4-oxo-2-phenyl-2,3,4,5-tetrahydro-1,5-benzothiazepine-5-acetamide as obtained in (iv) of Example 23 and 0.5 g of succinimido 2-indolecarboxylate, 0.2 g of cis-8 chloro-3-(2-indolecarboxamido)- 4-oxo-2-phenyl-2,3,4,5-tetrahydro-1,5-benzothiazepine-5-acetamide is obtained, m.p. 174°–178° C.

NMR spectrum (CDC$_3$; ppm): δ=4.60 (m, 2H), 5.10 (t, 1H), 5.28 (d, 1H), 6.49 (1H), 7.1–7.6 (m, 15H), 7.8 (1H).

EXAMPLE 28

By conducting the same reaction and treatment as in (v) of Example 13 using 0.3 g of trans-3-amino-8-chloro-4-oxo-2-phenyl-2,3,4,5-tetrahydro-1,5-benzothiazepine-5-acetamide as obtained in (ii) of Example 24 and 0.5 g of succinimido 2-indolecarboxylate, 0.17 g of trans-8-chloro-3-(2-indolecarboxamido)-4-oxo-2-phenyl-2,3,4,5-tetrahydro-1,5-benzothiazepine-5-acetamide is obtained, m.p. 274°–278° C.

NMR spectrum (CDCl$_3$+CD$_3$OD;ppm): δ=4.18 (d, 1H), 4.70 (d, 1H), 4.84 (d, 1H), 5.15 (d, 1H), 6.9–7.6 (m, 13H).

EXAMPLE 29

(i) In 550 ml of dried tetrahydrofuran containing 1 ml of methanol is dissolved dimethyl 2-amino-2-[2-(2-nitrophenyl)-1phenylethyl]propanedicarboxylate obtained in accordance with a known method, whereto 6.86 g of 60% sodium hydride is added while stirring. The reaction mixture is heated to 40° C. After the termination of generation of hydrogen gas, 28.4 g of O-(2,4-dinitrophenyl)hydroxylamine obtained in accordance with a known method is added thereto under ice-cooling and the mixture is stirred for 2 hours. To a red-yellow solid obtained after the solvent is distilled off is added 600 ml of chloroform and the mixture is stirred well. Then, the insoluble producet is filtered off. The filtrate is concentrated and isopropyl ether and hexane are added to the residue. The separated solid is collected by filtration to give 36.7 g of dimethyl 2-amino-2-[2-(2-nitrophenyl)-1phenylethyl]propanedicarboxylate, m.p. 114° C.

NMR spectrum (CDC$_3$; ppm): δ=2.20 (brs, 2H), 3.52 (s, 3H), 3.80 (s, 3H), 6.9–7.4 (8H), 7.6–7.8 (1H).

(ii) In 1000 ml of acetic acid is dissolved 42.45 g of dimethyl 2-amino-2-[2-(2-nitrophenyl)-1-phenylethyl]-propanedicarboxylate, whereto 55.6 g of zinc is added while stirring at temperature of 70–85° C. After stirring for 2 more hours, 750 ml of acetic acid is added thereto and the precipitate is filtered off. After the filtrate is concetrated under reduced pressure, a saturated aqueous solution of potassium carbonate is added and organic substance is extracted from chloroform. After the chloroform layer is dried and concentrated, isopropyl ether and hexane is added thereto, and the separated crystals are collected by filtration to give 22.1 g of 3-amino-3-methoxycarbonyl-4-phenyl-1,3,4,5-tetrahydro-1-benzazepin-2(2H)-one, m.p. 201° C.

NMR spectrum (CDC$_3$; ppm): δ=3.12 (dd, 1H, J=3Hz, 16Hz), 3.37 (dd, 1H, J ™ 3Hz, 10Hz), 3.56 (s, 3H), 4.00 (dd, 1H, J=10Hz, 16Hz), 6.9–7.4 (9H), 8.10 (brs, 1H).

(iii) A mixture of 17.98 g of 3-amino-3-methoxycarbonyl-4-phenyl-1,3,4,5-tetrahydro-1-benzazepin-2(2H)-one, 21.76 g of lithium iodide trihydrate and 400 ml of dried pyridine is stirred under reflux for 2 days. To the residue obtained after the mixture is concentrated under reduced pressure, an aqueous solution of potassium carbonate, an aqueous solution of sodium thiosulfate and chloroform are added, and the organic substance is extracted. The chloroform layer is dried and concentrated. The obtained residue is subjected to silica gel chromatography (eluent: chloroform:methanol =20:1) to give 5.6 g of cis-3-amino-4-phenyl-1,3,4,5-tetrahydro-1-benzazepin-2(2H)-one and 5.44 g of trans-3-amino-4-phenyl-1,3,4,5-tetrahydro-benzazepin-2(2H)-one.

Cis form:
NMR spectrum (CDC$_3$; ppm): δ=1.30 (brs, 2H), 2.7–3.3 (2H), 3.5–3.9 (2H), 6.9–7.6 (9H), 8.20 (brs, 2H).

Trans form:
NMR spectrum (CDC$_3$; ppm): δ=2.1 (2H), 2.66 (d, 1H, J=13Hz), 3.1–3.6 (2H), 3.76 (d, 1H, J=11Hz), 6.8–7.5 (10H).

(iv) In 100 ml of dried dimethylformamide is dissolved 5.55 g of cis-3-amino-4-phenyl-1,3,4,5-tetrahydro-1-benzazepin-2(2H) one and 0.97 g of 60% sodium hydride is added at room temperature. After stirring for 30 minutes, a solution of 2.7 ml of ethyl bromoacetate in 10 ml of dimethylformamide is added dropwise under cooling with ice for 30 minutes. The reaction temperature is slowly elevated to room temperature. After stirring for 15 hours, the reaction mixture is concentrated under reduced pressure. Water and chloroform are poured to the obtained residue and organic substance is extracted. The chloroform layer is dried and concentrated. The obtained oily product is subjected to silica gel chromatography (eluent: chloroform:methanol=20:1) to give 0.6 g of ethyl cis-3-amino-2-oxo-4-phenyl-2,3,4,5-tetrahydro-1H-1-benzazepine-1-acetate.

NMR spectrum (CDC$_3$; ppm): δ=1.28 (t, 3H, J=7Hz), 1.47 (brs, 2H), 2.7–3.1 (1H), 3.4–3.9 (3H), 4.23 (q, 2H, J=7Hz), 4.21 (d, 1H, J=16Hz), 4.88 (d, 1H, J=16Hz), 7.0–7.5 (9H).

(v) By conducting the same reaction and treatment as in (v) of Example 1 using 6.3 g of ethyl cis-3-amino-2-oxo-4-phenyl-2,3,4,5-tetrahydro-1H-1-benzazepine-1-acetate dissolved in 250 ml of methanol, 5.5 g of cis-3-amino-2-oxo-4-phenyl-2,3,4,5-tetrahydro-1H-1-benzazepine-1-acetamide is obtained.

NMR spectrum (CDC$_3$; ppm): δ=1.48 (brs, 2H), 2.7 3.8 (4H), 4.34 (d, 1H, J=16Hz), 4.68 (d, 1H, J=16Hz), 5.70 (br, 1H), 6.25 (br, 1H), 7.0–7.5 (9H).

(vi) By conducting the reaction and treatment in the same manner as in Example 12 using 0.2 g of cis-3-amino-2-oxo-4-phenyl-2,3,4,5-tetrahydro-1H-1-benzazepine 1-acetamide and 0.1 g of succinimido 2 indolecarboxylate dissolved in 5 ml of dimethylformamide and recrystallization from a mixed solvent of ethanol and isopropyl alcohol, 0.18 g of cis-3-(2-indolecarboxamido)-2-oxo-4-phenyl-2,3,4,5-tetrahydro-1H-1-benzazepine-1-acetamide ½ isopropyl alcohol adduct is obtained, m.p. 204°–216° C.

NMR spectrum (DMSO-d$_6$; ppm): δ=2.91 (m, 1H), 4.36 (d, 1H, J=17Hz), 4.66 (d, 1H, J=17Hz), 6.55 (1H).

EXAMPLE 30

(i) By conducting the same reaction and treatment as in (iv) of Example 29 using 5.3 g of trans-3-amino-4-phenyl-1,3,4,5-tetrahydro-1-benzazepin-2(2H)-one as obtained in (iii) of Example 29 and ethyl bromoacetate, 0.55 g of ethyl trans-3-amino-2-oxo-4-phenyl-2,3,4,5-tetrahydro-1H-1-benzazepine-1-acetate is obtained.

NMR spectrum (CDC$_3$; ppm): δ=1.27 (t, 3H, J=7Hz), 1.84 (brs, 2H), 2.58 (d, 1H, J=14Hz), 3.25 (dd, 1H, J=8Hz, 11Hz), 3.78 (d, 1H, J=11Hz), 3.83 (dd, 1H, J=8Hz, 14Hz), 4.19 (q, 2H, J=7Hz), 4.41 (d, 1H, J=17Hz), 4.78 (d, 1H, J=17Hz), 6.8–7.5 (9H).

(ii) By conducting the same reaction and treatment as in (v) of Example 1 using 4.8 g of ethyl trans-3-amino-2-oxo-4-phenyl-2,3,4,5-tetrahydro-1H-1-benzazepine-1-acetate dissolved in 200 ml of methanol, 2.63 g of trans-3-amino-2-oxo-4-phenyl-2,3,4,5-tetrahydro-1H-1-benzazepine-1-acetamide is obtained.

NMR spectrum (CDC$_3$; ppm): δ=1.63 (2H), 2.59 (d, 1H, J=13Hz), 3.1–3.8 (2H), 3.80 (d, 1H, J=11Hz), 4.23 (d, 1H, J=15Hz), 4.71 (d, 1H, J=15Hz), 5.7 (br, 1H), 6.4 (br, 1H), 6.8–7.5 (9H).

(iii) In 5 ml of dimethylformamide are dissolved 0.2 g of trans-3-amino-2-oxo-4-phenyl 2,3,4,5-tetrahydro-1H-1-benzazepine-1-acetamide and 0.18 g of succinimido 2-indolecarboxylate, and the same reaction and treatment as in Example 12 is carried out to give 0.2 g of trans-3-(2-indolecarboxamido)-2-oxo-4-phenyl-2,3,4,5-tetrahydro-1H-1-benzazepine-1-acetamide, m.p. 280°–283° C. (decomposition).

NMR spectrum (DMSO-d$_6$; ppm): δ=4.28 (d, 1H, J=17Hz), 4.67 (d, 1H, J=17Hz), 8.63 (d, 1H, J=8Hz).

EXAMPLE 31

In 50 ml of dichloromethane are dissolved 2.42 g of cis-3-amino-2-oxo-4-phenyl-2,3,4,5-tetrahydro-1H-1-benzazepine-1-acetamide as obtained in (v) of Example 29 and 1.9 g of succinimido γ-butyrolactone-γ(S)-carboxylate, and the same reaction and treatment as in (vi) of Example 1 is carried out to give 2.53 g of cis-3-[γ-butyrolactone-γ(S)-caboxamido]-2-oxo-4-phenyl-2,3,4,5-tetrahydro-1H-1-benzazepine-1-acetamide.

NMR spectrum (CDC$_3$; ppm): δ=1.7–2.5 (4H), 2.9 (1H), 3.65 (1H), 4.0 (1H), 4.4–4.8 (4H), 7.2.–7.4 (9H).

EXAMPLE 32

In 35 ml of dichloromethane are dissolved 1.70 g of trans-3-amino-2-oxo-4-phenyl-2,3,4,5-tetrahydro 1H 1-benzazepine-1-acetamide as obtained in (ii) of Example 30 and 1.33 g of succinimido γ-butyrolactone-γ(S)-carboxylate, and the same reaction and treatment as in (vi) of Example 1 is carried out to give 1.65 g of trans-3-[γ-butyrolactone-γ(S)caboxamido]-2-oxo-4-phenyl-2,3,4,5-tetrahydro-1H-1-benzazepine-1-acetamide.

NMR spectrum (CDCl$_3$-DMSO-d$_6$; ppm): δ=1.7–2.5 (4H), 2.7 (1H), 3.6 (1H), 3.8 (1H), 4.3–5.0 (4H), 6.3 (1H), 6.9–7.9 (11H).

EXAMPLE 33

In 50 ml of dimethylformamide are dissolved 2.53 g of cis-3-amino-2-oxo-4-phenyl-2,3,4,5-tetrahydro-1H-1-benzazepine-1-acetamide as obtained in (v) of Example 29 and 1.06 g of L-pyroglutamic acid, and the same reaction and treatment as in Example 3 is carried out to give 2.41 g of cis-2-oxo-3-[5-oxo-2(S)-pyrrolidinecarboxamido]-4-phenyl-2,3,4,5-tetrahydro-1H-1-benzazepine-1-acetamide.

NMR spectrum (CDC$_3$; ppm): δ=1.5-2.3 (4H), 2.9 (1H), 3.5 (1H), 3.8-4.0 (2H), 4.3-4.7 (3H), 5.8-6.8 (4H), 7.1-7.5 (9H).

EXAMPLE 34

In 20 ml of dimethylformamide are dissolved 1.00 g of trans-3-amino-2-oxo-4-phenyl-2,3,4,5-tetrahydro-1H-1-benzazepine-1-acetamide as obtained in (ii) of Example 30 and 0.42 g of L-pyroglutamic acid, and the same reaction and treatment as in Example 3 is carried out to give A isomer (0.41 g) and B isomer (0.42 g) of trans-2-oxo-3-[5-oxo-2(S)-pyrrolidinecarboxamido]-4-phenyl-2,3,4,5-tetrahydro-1H-1-benzazepine-1-acetamide.

A isomer:

NMR spectrum (CDC$_3$; ppm): δ=1.9-2.2 (4H), 2.66 (d, 1H, J=14Hz), 3.6 (2H), 3.96 (1H), 4.19 (d, 1H, J=17Hz), 4.69 (d, 1H, J=17Hz), 4.88 (1H), 6.5 (br, 1H), 6.9-7.4 (1H), 7.9 (br, 1H)

$[α]_D$ = +217.6° (c=0.1%, DMSO).

B isomer:

NMR spectrum (CDC$_3$; ppm): δ=1.45 (1H), 2.1-2.3 (3H), 2.75 (d, 1H, 14Hz), 3.52 (dd, 1H, J=9Hz, 14Hz), 3.67 (dd, 1H, J=9Hz, 12Hz), 3.98 (1H), 4.04 (d, 1H, J=17Hz), 4.70 (d, 1H, J=17Hz), 5.12 (dd, 1H, J=9Hz, 12Hz), 6.1 (1H), 6.8 (1H), 7.1-7.4 (9H), 7.7 (1H), 8.1 (d, 1H, J=9Hz).

$[α]_D$ = −119° (c=0.1%, DMSO).

EXAMPLE 35

(i) To 13 g of ethyl trans-3-amino-4-oxo-2-phenyl-2,3,4,5-tetrahydro-1,5-benzothiazepine-5-acetate as obtained in (iv) of Example 1 and 5.95 g of D-10-camphorsulfonic acid is added 200 ml of ehtyl acetate, and the mixture is dissolved under heating. The precipitated crystals are cooled and then collected by filtation to give 9.7 g of a salt. To the salt is added 50 ml of an aqueous solution of sodium hydrogen-carbonate and extracted with chloroform (100 ml, three times). To the residue which is obtained by distilling off the solvent is added 2.7 g of D-10-camphorsulfonic acid followed by dissolving in 100 ml of ethyl acetate under heating. The precipitated crystals are cooled and collected by filtation to give 5.5 g of ethyl 3(R)-amino-4-oxo-2(S)-phenyl-2,3,4,5-tetrahydro-1,5-benzothiazepine-5-acetate D-10-camphorsulfonate, m.p. 204°-206° C.

$[α]_D$ = −345° (c=0.1%, DMSO).

(ii) To 5.5 g of ethyl 3(R)-amino-4-oxo-2(S)-phenyl-2,3,4,5-tetrahydro-1,5-benzothiazepine-5-acetae D-10-camphorsulfonate is added 50 ml of an aqueous solution of sodium hydrogencarbonate and extracted with chloroform (100 ml, three times). The residue which is obtained by distilling off the solvent is dissolved in 50 ml of methanol and saturated with ammonia under cooling. After allowing to stand overnight, the solvent is distilled off to give 2.0 g of ethyl 3(R)-amino-4-oxo-2(S)-phenyl-2,3,4,5-tetrahydro-1,5-benzothiazepine-5-acetate, m.p. 176°-178° C.

$[α]_D$ = −661° (c=0.1%, DMSO).

(iii) To a solution of 10 ml of dry dimethylformamide of 511 mg of ethyl 3(R)-amino-4-oxo-2(S)-phenyl-2,3,4,5-tetrahydro-1,5-benzothiazepine-5-acetate, 200 mg of 3-cyclopentanone-1(R)-carboxylic acid which is prepared according to the known procedure and 322 mg of 1-hydroxybenzotriazole is added 322 mg of dicyclohexylcarbodiimide. After allowing to stand overnight, the precipitated dicyclohexylurea is filtered off. The dimethylformamide was distilled off under reduced pressure, and to the residue is added chloroform. After washing with an aqueous solution of sodium chloride and drying over magnesium sulfate, the solvent is distilled off. The residue is subjected to column chromatography on silica gel and crystallized from benzene to give 540 ml of 3(R)-[3-cyclopentanone-1(R)-carboxamido]-4-oxo-2(S)-phenyl-2,3,4,5-tetrahydro-1,5-benzothiazepine-5-acetamide, m.p.=135°-150° C.

NMR spectrum (CDCL$_3$; ppm) =1.8-2.4 (6H), 2.74 (m, 1H), 4.41 (d, 1H, J=11.7Hz), 4.47 (d, 1H, J=17.1Hz), 4.67 (d, 1H, J=17.1Hz), 5.02 (dd, 1H, J=7.8Hz, 11.7Hz), 5.9 (br, 1H), 6.6 (br, 1H), 7.0-7.7 (10H).

$[α]_D$ = −494° (c=0.1%, DMSO).

EXAMPLE 36

To a solution of cis-3-amino-8-chloro-4-oxo-2-phenyl-2,3,4,5-tetrahydro-1,5-benzothiazepine-5-acetamide as obtained in (iv) of Example 23, 0.69 g of 3-cyclopentane-1(R)-carboxylic acid which can be obtained according to the known manner and 0.88 g of 1-hydroxybenzotriazole in 30 ml of dry dimethylformamide is added 1.12 g of dicyclohexylcarbodiimide. After allowing to stand overnight, the precipitated dicyclohexylurea is filtered off. The dimethylformamide is distilled off, and to the residure is added chloroform followed by washing with an aqueous solution of sodium chloride and drying over magnesium sulfate. A part of the residue obtained by distilling off the solvent is subjected to column chromatography on silica gel to give cis-8-chloro-3-[3-cyclopentanone-1(R)-carboxamido]-4-oxo-2-phenyl-2,3,4,5-tetrahydro-1,5-benzothiazepine-5-acetamide. A isomer: 170 mg; B isomer: 280 mg.

A isomer: m.p. 145°-150° C.

NMR spectrum (CDCL ; ppm) =1.6-2.4 (6H), 2.68 (m, 1H), 4.5 (2H), 4.87 (dd, 1H), 5.24 (d, 2H, J=7.3Hz), 6.0 (br, 1H), 6.24 (d, 1H), 6.9 (br, 1H), 7.2-7.6 (7H), 7.78 (d, 2H, J=2.4Hz).

$[α]_D$ = +130° (c=0.1%, DMSO).

B isomer: m.p. 210° C.

NMR spectrum (CDCL$_3$; ppm) =1.9-2.4 (6H), 2.64 (m, 1H), 4.5 (2H), 4.87 (dd, 1H), 5.22 (d, 1H, J=7.3Hz), 5.7 (br, 1H), 6.07 (d, 1H), 6.9 (br, 1H), 7.2-7.6 (7H), 7.78 (d, 1H, J=2.5Hz)

$[α]_D$ = −106° C. (c=0.1%, DMSO).

The present invention has been fully explained in the description and examples given above, but any variations and modifications thereof may be made without departing from the spirit and scope of the present invention.

What is claimed is:

1. A benzolactam compound of the formula

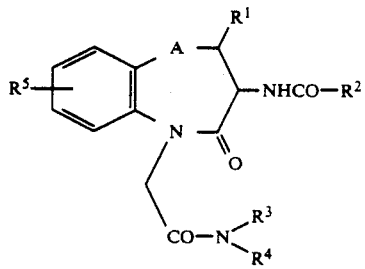

wherein A is sulfur atom, oxygen atom, methylene group, —NR$^6$— group (wherein R$^6$ is hydrogen atom, an alkyl group having 1 to 6 carbon atoms which may have unsaturated bond, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms or benzyloxycarbonyl, tert-butoxycarbonyl or trifluoroacetyl) or carbonyl group; $R^1$ is hydrogen atom, an alkyl group having 1 to 6 carbon atoms which may have unsaturated bond, a cycloalkyl group having 5 to 7 carbon atoms which may contain double bond on the ring, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms, and an alkoxy group having from 1 to 6 carbon atoms, a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and a alkoxy group having 1 to 6 carbon atoms or an alkyl group having 1 to 6 carbon atoms which is substituted by at least one a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms, $R^2$ is an alkyl group having 1 to 6 carbon atoms which may have unsaturated bond, a cycloalkyl group having 5 to 7 carbon atoms which may contain double bond on the ring, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, trifluoromethyl, chloromethyl or 2,2,2-trifluoroethyl, an alkoxy group having 1 to 6 carbon atoms which may be substituted by phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms, an alkyl group having 1 to 6 carbon atoms which is substituted by at least one a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms or a group representable by the formula

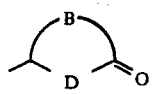

which may be fused by phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms or a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms wherein B is an alkylene having 1 to 6 carbon atoms which may further be substituted by an alkyl group having 1 to 4 carbon atoms, propylidene, butylidene, vinylene, propenylene, —$CH_2OCH_2$—, —$CH_2S(O)_nCH_2$— (n represents an integer of 0 to 2), —$CH_2CON(R^8)$— (wherein $R^8$ is hydrogen atom or an alkyl group having 1 to 6 carbon atoms) and D is oxygen atoms, methylene group or —$N(R^9)$— (wherein $R^9$ is hydrogen atom or an alkyl group having 1 to 6 carbon atoms); $R^3$ and $R^4$ are the same or different and are independently hydrogen atom, an alkyl group having 1 to 6 carbon atoms which may have unsaturated bond, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms or a group which is combined with each other together with the adjacent nitrogen atom to form a heterocycle selected from 1-pyrrolidinyl, piperidino, morpholino and 1-piperazinyl, which may be substituted by an alkyl or aralkyl group and $R^5$ is hydrogen atom or one to three halogen atom(s), alkyl group(s) having 1 to 6 carbon atoms which may have unsaturated bond or alkyl group(s) having 1 to 6 carbon atoms which may be substituted by phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms (when $R^5$ is two to three atoms and/or groups, the atoms and/or the groups are the same or different), or an isomer thereof or a pharmaceutically acceptable salt thereof.

2. A benzolactam compound as claimed in claim 1, wherein said compounds are trans-3(S)-[γ-butyrolactone-γ(S)-carboxamido]-4-oxo-2(R)-phenyl-2,3,4,5-tetrahydro-1,5-benzothiazepine-5-acetamide, trans-3(R)-

[γ-butyrolactone-γ(S)-carboxamido]-4-oxo-2(S)-phenyl-2,3,4,5-tetrahydro-1,5-benzothiazepine-5-acetamide, cis-3-[γ-butyrolactone-γ(S)-carboxamido]-4-oxo-2 phenyl-2,3,4,5-tetrahydro-1,5-benzothiazepine-5-acetamide, trans-4-oxo-3-[5-oxo-2(S)-pyrrolidinecarboxamido]-2-phenyl-2,3,4,5-tetrahydro-1,5-benzothiazepine-5-acetamide, trans-3-(2-indolecarboxamido)-4-oxo-2-phenyl2,3,4,5-tetrahydro-1,5-benzothiazepine-5-acetamide, trans-3-(4,5-dihydroorotylamino)-4-oxo-2-phenyl-2,3,4,5-tetrahydro-1,5-benzothiazepine-5-acetamide, 2-isopropyl-3-(2-indolecarboxamido)-4-oxo-2,3,4,5-tetrahydro-1,5-benzothiazepine- 5 -acetamide, 3(R)-[γ-butyrolactone-γ(S)-carboxamido]-4-oxo-2,3,4,5-tetrahydro-1,5-benzothiazepine-5acetamide, trans-3-[γ-bulyrolactone-γ(S)-carboxamido]-4-oxo-2-(2-thienyl)-2,3,4,5-tetrahydro-1,5-benzothiazepine-5-acetamide, trans-3-(2-indolecarboxamido)-4-oxo-2 (2-thienyl)-2,3,4,5-tetrahydro-1,5-benzothiazepine-5-acetamide, trans- 3-(2 indolecarboxamido)-4-oxo-2-phenyl-N-(2-phenylethyl)-2,3,4,5-tetrahydro-1,5-benzothiazepine 5-acetamide, trans-3-(2-indolecarboxamido)-2-phenyl-5-(1-pyrrolidinylcarbonylmethyl)-2,3-dihydro-1,5-benzothiazepin-4(5H)-one, cis-4-oxo-3(R)-[5-oxo-2(S)-pyrrolidinecarboxamido]-2(R)-phenyl-2,3,4,5-tetrahydro-1,5-benzothiazepine-5-acetamide, cis-4-oxo-3(S)-[5-oxo-2(S)-pyrrolidinecarboxamido]-2(S)-phenyl-2,3,4,5-tetrahydro-1,5-benzothiazepine-5-acetamide, cis-3-[γ-butyrolactone-γ(S)-carboxamido]-8-chloro-4-oxo-2-phenyl-2,3,4,5-tetrahydro-1,5-benzothiazepine-5-acetamide, trans-3-[γ-butyrolactone-γ(S)-carboxamido]-8-chloro-4-oxo-2-phenyl- 2,3,4,5-tetrahydro-1,5-benzothiazepine-5-acetamide, cis-3-(2-indolecarboxamido)-2-oxo-4-phenyl-2,3,4,5-tetrahydro-1H-1-benzazepine-1-acetamide and trans-3-(2-indolecarboxamido)-2-oxo-4-phenyl-2,3,4,5-tetrahydro-1-1-benzazepine-1-acetamide, or an isomer thereof as well as a pharmaceutically acceptable salt thereof.

3. A pharmaceutical composition as a brain-function improving and brain function-treating agent which comprises a therapeutically effective amount of the benzolactam compound as claimed in claim 1 or 2 with a pharmaceutically acceptable additive.

4. A benzolactam compound of the formula

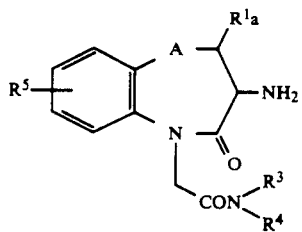

wherein A is sulfur atom, oxygen atom, methylene group, —NR6— group (wherein R6 is hydrogen atom, an alkyl group having 1 to 6 carbon atoms which may have unsaturated bond, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms or benzyloxycarbonyl, tert-butoxycarbonyl or trifluoroacetyl) or carbonyl group; wherein R1a is an alkyl group having 1 to 6 carbon atoms which may have unsaturated bond, a cycloalkyl group having 5 to 7 carbon atoms which may contain double bond on the ring, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms or an alkyl group having 1 to 6 carbon atoms which is substituted by at least one monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms, and each of the other symbols is as defined in claim 1, an isomer thereof or a pharmaceutically acceptable acid addition salt thereof.

5. A benzolactam compound as claimed in claim 4, wherein said compounds are 3(R)-[3-cyclopentanone-1(R)-carboxamido]-4-oxo-2(S)-phenyl-2,3,4,5-tetrahydro-1,5-benzothiazepine-5-acetamide and cis-8-chloro-3-[3-cyclopentanone-1(R)-carboxamido]-4-oxo-2-phenyl-2,3,4,5-tetrahydro- 1,5-benzothiazepine-5-acetamide, or an isomer thereof as well as a pharmaceutically acceptable salt thereof.

6. A diuretic composition which comprises a therapeutically effective amount of the benzolactam compound as claimed in claim 4 or 5 with a pharmaceutically acceptable additive.

7. An antiulcer composition which comprises a therapeutically effective amount of the benzolactam compound as claimed in claim 4 or 5 with a pharmaceutically acceptable additive.

8. A benzolactam compound of the formula

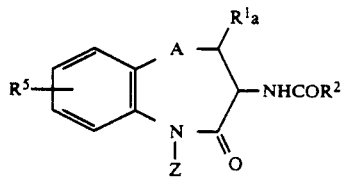

wherein Z is a group of the formula: —CH2CO2O, wherein Q is a carboxy-protecting group, an isomer thereof or a pharmaceutically acceptable acid addition salt thereof wherein A is sulfur atom, oxygen atom, methylene group, —NR6— group (wherein R6 is hydrogen atom, an alkyl group having 1 to 6 carbon atoms which may have unsaturated bond, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms or benzyloxycarbonyl, tert-butoxycarbonyl or trifluoroacetyl) or carbonyl group; $R^2$ is an alkyl group having 1 to 6 carbon atoms which may have unsaturated bond, a cycloalkyl group having 5 to 7 carbon atoms which may contain double bond on the ring, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, trifluoromethyl, chloromethyl or 2,2,2-trifluoroethyl, an alkoxy group having 1 to 6 carbon atoms which may be substituted by phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thizolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms, an alkyl group having 1 to 6 carbon atoms which is substituted by at least one a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms or a group representable by the formula

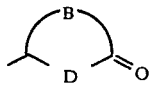

which may be fused by phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms or a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms wherein B is an alkylene having 1 to 6 carbon atoms which may further be substituted by an alkyl group having 1 to 4 carbon atoms, propylidene, butylidene, vinylene, propenylene, —$CH_2OCH_2$—, —$CH_2S(O)_nCH_2$— (n represents an integer of 0 to 2), $CH_2CON(R^8)$— (wherein $R^8$ is hydrogen atom or an alkyl group 1 to 6 carbon atoms) and D is oxygen atom, or —N($R^9$)— (wherein $R^9$ is hydrogen atom or an alkyl group having 1 to 6 carbon atoms); $R^5$ is hydrogen atom or one to three halogen atom(s), alkyl group(s) having 1 to 6 carbon atoms which may have unsaturated bond or alkyl group(s) having 1 to 6 carbon atoms which may be substituted by phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms (when $R^5$ is two to three atoms and/or groups, the atoms and/or the groups are the same or different); $R^1a$ is an alkyl group having 1 to 6 carbon atoms which may have unsaturated bond, a cycloalkyl group having 5 to 7 carbon atoms which may contain double bond on the ring, an alkyl group having 1 to 6 carbon atoms substituted by at least one of phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, phenyl, 1-naphthyl or 2-naphthyl which may have on the aromatic ring at least one substituent selected from among halogen, trifluoromethyl, hydroxy, amino, nitro, cyano, an alkyl group having 1 to 6 carbon atoms and an alkoxy group having 1 to 6 carbon atoms, a monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms or an alkyl group having 1 to 6 carbon atoms which is substituted by at least one monocyclic or polycyclic aromatic ring containing 1 to 3 nitrogen atom(s), oxygen atom(s) and/or sulfur atom(s) selected from thienyl, furyl, pyrrolyl, pyrazolyl, imidazolyl, thiazolyl, oxazolyl, pyridyl, quinolyl, isoquinolyl, benzimidazolyl, benzothiazolyl or indolyl, which may have on the aromatic ring at least one substituent selected from among halogen, amino, an alkyl group having 1 to 6 carbon atoms and an alkoxy group having 1 to 6 carbon atoms, and A is as defined above.

* * * * *